(12) United States Patent
Yatvin et al.

(10) Patent No.: US 6,387,876 B1
(45) Date of Patent: May 14, 2002

(54) COVALENT POLAR LIPID-CONJUGATES WITH BIOLOGICALLY ACTIVE COMPOUNDS FOR USE IN SALVES

(75) Inventors: Milton B. Yatvin, Portland, OR (US); Michael HB Stowell, Padadena, CA (US)

(73) Assignee: Oregon Health and Science University, Portland, OR (US)

( * ) Notice: Subject to any disclaimer, the term of this patent is extended or adjusted under 35 U.S.C. 154(b) by 0 days.

(21) Appl. No.: 09/415,640

(22) Filed: Oct. 12, 1999

Related U.S. Application Data

(63) Continuation of application No. 08/685,152, filed on Jul. 23, 1996, now Pat. No. 5,965,519, which is a continuation-in-part of application No. 08/142,771, filed on Oct. 26, 1993, now Pat. No. 5,543,389, which is a continuation-in-part of application No. 07/911,209, filed on Jul. 9, 1992, now Pat. No. 5,256,641, which is a continuation-in-part of application No. 07/607,982, filed on Nov. 1, 1990, now Pat. No. 5,149,794.

(51) Int. Cl.$^7$ .................. A61K 38/00; A61K 31/70; A61K 31/685

(52) U.S. Cl. .................. 514/2; 514/51; 514/78

(58) Field of Search .................. 514/2, 51, 78

(56) References Cited

U.S. PATENT DOCUMENTS

| | | |
|---|---|---|
| 5,149,794 A | 9/1992 | Yatvin et al. |
| 5,256,641 A | 10/1993 | Yatvin et al. |
| 5,543,389 A | 8/1996 | Yatvin et al. |
| 6,090,800 A | * 7/2000 | Unger et al. |

OTHER PUBLICATIONS

Menger et al., "Synthesis of a Lipid/Peptide/Drug Conjugate: N4-(Acylpeptidyl)-Ara-C", Bioconj. Chem. (1994) vol. 5, pp. 162-166.*

Henrikus and Kampffmeyer, "Ester hydrolysis conjugation reactions in intact skin and skin homogenate, and by liver esterase of rabbits," *Xenobiotica* 22: 1357-1366 (1992).

Heymann et al., "Organophosphate Sensitive and Insensitive Carboxylesterases in Human Skin," *Chem. Biol. Interactions* 87: 217-226 (1993).

Hopp, "Immunogenicity of a Synthetic HBsAg Peptide: Enhancement by Conjugation to a Fatty Acid Carrier," *Mol. Immunol.* 21: 13-16 (1984).

Jardetzky et al., "Identification of self peptides bound to purified HLA-B27," *Nature* 353: 326-329 (1991).

Kubota et al., "Metabolism and Degradation of Betamethasone 17-Valerate in Homogenized Living Skin Equivalent," *Dermatology* 188: 13-17 (1994).

Lamont et al., "The use of Peptide Analogs with Improved Stability and MHC Binding Capacity to Inhibit Antigen Presentation In Vitro and In Vivo," *J. Immunol.* 144: 2493-2498 (1990).

Lanzavecchia et al., "Irreversible assocation of peptides with class II MHC molecules in living cells," *Nature* 357: 249-252 (1992).

Lee et al., "Antibacterial peptides from pig intestines: Isolation of a mamalian cecropin," *Proc. Natl. Acad. Sci. USA* 86: 9159-9162 (1989).

Lehrer et al., "Defensins: Endogenous Antibiotic Peptides of Animal Cells," *Cell* 64: 229-230 (1991).

Lipozenčic et al., "Langerhans cells in the immunopathology of contact allergic dermatitis," *Eur. J. Histochem* 38: 303-310 (1994).

Matsuura et al., *J. Chem. Soc. Chem. Comm.* xx: 451-459 (1976).

Moehrle et al., "Aminopeptidase M and dipeptidyl peptidase IV activity in epithelial skin tumors: a histochemical study," *J. Cutaneous Pathology* 22: 241-247 (1995).

Mukhergee & Heidelberger, *Cancer Res.* 22: 815-822 (1962).

Parham, "Transporters of delight," *Nature* 348: 674-675 (1990).

Rahman et al., *Life Sci.* 31: 2061-2071 (1982).

Remy et al., *J. Org. Chem.* 27: 2491-2500 (1962).

Sadegh-Nasseri and Germain, "A role for peptide in determining MHC class II structure," *Nature* 353: 167-170 (1991).

Salord et al., *Biochim. Biophys. Acta* 886: 64-75 (1986).

SivaSai et al., "Effect of Recombinant Interferon Gamma Administration on Lesional Monocytes/Macrophages in Lepromatous Leprosy Patients," *Int. J. Leprosy & Other Mycobacterial Diseases* 61: 259-269 (1993).

Smith and Khorana, *J. Amer. Chem. Soc.* 80: 1141-1145 (1958).

(List continued on next page.)

Primary Examiner—Jon P. Weber
(74) Attorney, Agent, or Firm—Davidson, Davidson, Kappel, LLC

(57) ABSTRACT

This invention herein describes a method of facilitating the entry of drugs into cells and tissues at pharmokinetically useful levels and also a method of targeting drugs to specific organelles within the cell. This polar lipid/drug conjugate targeting invention embodies an advance over other drug targeting methods because through this method, intracellular drug concentrations may reach levels which are orders of magnitude higher than those achieved otherwise. Furthermore, it refines the drug delivery process by allowing therapeutic agents to be directed to certain intracellular structures. This technology is appropriate for use with antiproliferative, antibiotic, antimycotic, antiviral and antineoplastic drugs, in particular in combination with a multiplicity of other emollients and agents to make up topically-active substances such as salves, for rapid and efficient introduction of such agents through the epidermis for treatment of skin diseases and other disorders.

10 Claims, 23 Drawing Sheets

OTHER PUBLICATIONS

Wiesmüller et al., "The antibody response in BALB/c mice to the *Plasmodium falciparum* circumsporozoite repetitive epitope covalently coupled to synthetic lipopeptide adjuvant," *Immun.* 72: 109–113 (1991).

Zasloff, "Magainins, a class of antimicrobial peptides form Xenopus skin: Isolation, characterization of two active forms, and partial cDNA sequence of a precursor," *Proc. Natl. Acad. Sci USA* 84: 5449–5453 (1987).

Abbas et al., "Antigen Presentation and T Cell Antigen Recognition," *Cellular as J. Mol. Immunol.* (W.B. Saunders Co.; Philadelphia), pp. 116–136.

Barlow et al., "Mast cells and T lymphocytes in chronic urticaria," *Clinical & Experimental Allergy* 25: 317–322 (1995).

Boehnlein et al., "Characterization of Esterase and Alcohol Dehydrogenase Activity in Skin. Metabolism of Retinyl Palmitate to Retinol (Vitamin A) During Percutaneous Absorption," *Pharmaceutical Research* 11: 1155–1159 (1994).

Boman et al., "Cell–free immunity in Cecropia: A model system for antibacterial proteins," *Eur. J. Biochem.* 201: 23–31 (1990).

Bou–Gharios et al., "Expression of ectopeptidases in scleroderma," *Annals of Rheumatic Disease* 54: 111–116 (1995).

Brewster et al., "Improved Delivery through Biological Membranes XXXI: Solubilization and Stabilization of an Estradiol Chemical Delivery System by Modified β–Cyclodextrins," *J. Pharm. Sci.* 77: 981–985 (1985).

Brown et al., "Induction of Cell Surface Peptidase Activity: A Global Response to Cell Stress Correlated with Apoptosis," *J. Cellular Biochemistry* 54: 320–331 (1994).

Büyüktimkin et al., "Synthesis and Enhancing Effect of Dodecyl 2–(N,N–Dimethylamino)propionate on the Transepidermal Delivery of Indomethacin, and Clonidine, and Hydrocortisone," *Pharmaceutical Research* 10: 1632–1637 (1993).

Dachun et al., "Localization and Quantification of the Non-specific Esterase in Injured Skin for Timing of Wounds," *Forensic Science International* 53: 203–213 (1992).

De Magistris et al., "Antigen Analog–Major Histocompatibility Complexes Act As Antagonists of the T Cell Receptor," *Cell* 68: 625–634 (1992).

Elliott et al., "Naturally processed peptides," *Nature* 348: 195–197 (1990).

Falk et al., "Cellular peptide composition governed by major histocompatibility complex class I molecules," *Nature* 348: 248–251 (1990).

Faustman et al., "Linkage of Faulty Major Histocompatibility Complex Class I to Autoimmune Diabetes," *Science* 254: 1756–1776 (1991).

Frisch et al., "Parameters affecting the immunogenicity of a liposome–associated synthetic hexapeptide antigen," *Eur. J. Immun.* 21: 185–193 (1991).

Germain & Hendrix, "MHC class II structure, occupancy and surface expression determined by post–endoplasmic reticulum antigen binding," *Nature* 353: 134–139 (1991).

Guéry et al., "Selective Immunosuppression by Administration of Major Histocompatibility Complex (MHC) Class II–Binding Peptides. I. Evidence for In Vivo MHC Blockade Preventing T Cell Activation," *J. Exp. Med.* 175: 1345–1352 (1992).

* cited by examiner

CORNIFIED LAYER →

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO: 1:

Gly Gly Gly Gly
1

(2) INFORMATION FOR SEQ ID NO: 2:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO: 2:

Ala Ala Ala Ala
1

(2) INFORMATION FOR SEQ ID NO: 3:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO: 3:

Gly Ser His Leu Val Glu Ala Leu
1              5

(2) INFORMATION FOR SEQ ID NO: 4:

```
        (i) SEQUENCE CHARACTERISTICS:
            (A) LENGTH: 8 amino acids
            (B) TYPE: amino acid
            (D) TOPOLOGY: linear (ii) MOLECULE TYPE: peptide (xi) SEQUENCE DESCRIPTION: SEQ ID NO: 4:

His Leu Val Arg Ala Leu Tyr Leu
1               5

(2) INFORMATION FOR SEQ ID NO: 5:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (xi) SEQUENCE DESCRIPTION: SEQ ID NO: 5:

Val Glu Ala Leu Tyr Leu Val Cys
1               5

(2) INFORMATION FOR SEQ ID NO: 6:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (xi) SEQUENCE DESCRIPTION: SEQ ID NO: 6:

Glu Ala Leu Tyr Leu Val Cys Gly
1               5

(2) INFORMATION FOR SEQ ID NO: 7:

(i) SEQUENCE CHARACTERISTICS:
            (A) LENGTH: 31 amino acids
            (B) TYPE: amino acid
            (D) TOPOLOGY: linear (ii) MOLECULE TYPE: peptide (xi) SEQUENCE DESCRIPTION: SEQ ID NO: 7:

Ala Xaa Cys Tyr Cys Arg Ile Pro Ala Cys Ile Ala Gly Asp Arg Arg
1               5                   10                  15

Tyr Gly Thr Cys Ile Tyr Gln Gly Arg Leu Trp Ala Phe Cys Cys
            20                  25                  30
```

COVALENT POLAR LIPID-CONJUGATES WITH BIOLOGICALLY ACTIVE COMPOUNDS FOR USE IN SALVES

This application is a continuation of U.S. patent application Ser. No. 08/685,152, filed Jul. 23, 1996, now U.S. Pat. No. 5,965,519, issued Oct. 12, 1999, which is a continuation-in-part of U.S. patent application Ser. No. 08/142,771, filed Oct. 26, 1993, now U.S. Pat. No. 5,543,389, issued Aug. 6, 1996, which is a continuation-in-part of U.S. patent application Ser. No. 07/911,209, filed Jul. 9, 1992, now U.S. Pat. No. 5,256,641, issued Oct. 26, 1993, which is a continuation-in-part of U.S. patent application Ser. No. 07/607,982, filed Nov. 1, 1990, now U.S. Pat. No. 5,149,794, issued Sep. 22, 1992, each of which are herein incorporated by reference.

BACKGROUND OF THE INVENTION

Field of the Invention

A major goal in the pharmacological arts has been the development of methods and compositions to facilitate the specific delivery of therapeutic and other agents to the appropriate cells and tissues that would benefit from such treatment, and the avoidance of the general physiological effects of the inappropriate delivery of such agents to other cells or tissues of the body. One common example of the need for such specificity is in the field of antiproliferative agent therapy for the treatment of skin diseases and disorders, in which the amount of a variety of antiproliferative agents to be safely administered topically or locally to a patient is limited by their systemic cytotoxic effects.

In addition, it is recognized in the medical arts that certain subcellular organelles are the sites of pharmacological action of certain drugs or are involved in the biological response to certain stimuli. Specific delivery of diagnostic or therapeutic compounds to such intracellular organelles is thus desirable to increase the specificity and effectiveness of such clinical diagnostic or therapeutic techniques. The invention provides polar lipid drug conjugates that target dermal, intradermal and infradermal structures in skin for delivery of therapeutic agents for the treatment of skin diseases and disorders.

Drug Targeting

It is desirable to increase the efficiency and specificity of administration of a therapeutic agent to the cells of the relevant tissues in a variety of pathological states. This is particularly important as relates to antiproliferative agents. Such agents typically have pleiotropic antibiotic and cytotoxic effects that damage or destroy uninvolved cells and tissues as well as cells and tissues comprising the pathological site. Thus, an efficient delivery system which would enable the delivery of such drugs specifically to the diseased or affected tissues cells would increase the efficacy of treatment and reduce the associated "side effects" of such drug treatments, and also serve to reduce morbidity and mortality associated with clinical administration of such drugs.

Numerous methods for enhancing the biological activity and the specificity of drug action have been proposed or attempted. To date, however, efficient or specific drug delivery remains to be predictably achieved.

An additional challenge in designing an appropriate drug delivery scheme is to include within the drug conjugate a functionality which could either accelerate or reduce the rate at which the drug is released upon arrival at the desired site. Such a functionality would be especially valuable if it allowed differential rates of drug release.

Medicinal salves and ointments for topical treatment purposes are known in the prior art for the treatment of a variety of pathological conditions. A multitude of pathological and other conditions have been treated by topical application of many classes of compounds in a variety of carriers, such as salves and ointments. However, carriers used in these conventional treatments are in no way specific for deposition of drugs, and suffer from non-specific deposition of the antiproliferative drug into both healthy and affected portions of the skin. Appropriate concentrations of topically-applied antiproliferative drugs, for example, are currently limited by the escape of the active agent(s) into the systemic circulation, with deleterious effects on other tissues and organs. An example of such a situation is the use of the drug methotrexate to treat psoriasis, where the amount of methotrexate that is capable of being topically applied is limited by hepato- and nephrotoxicity caused by systemic escape of the compound from the skin.

There remains a need in the art for an effective means for delivering biologically-active compounds, specifically drugs including antiproliferative drugs, to skin by topical administration of salves, ointments, and the like. Advantageous embodiments of such delivery means are formulated to efficiently deliver the biologically-active compound to the appropriate layer of the skin, while minimizing transit of the compound into the systemic circulation.

BRIEF SUMMARY OF THE INVENTION

The present invention is directed to an improved method for delivering biologically-active compounds, particularly drugs including preferably antiproliferative, antibiotic, antimycotic, antiviral and antineoplastic drugs, to cells comprising skin in animals in vivo and in vitro. This delivery system achieves specific delivery of such biologically-active compounds through conjugating the compounds with a polar lipid carrier. This invention has the specific advantage of facilitating the entry of such compounds into cells via a polar lipid carrier, achieving effective intracellular concentration of such compounds more efficiently and with more specificity than conventional delivery systems. The invention particularly provides pharmaceutical composition comprising the drug/polar lipid conjugates of the invention formulated with a medicinal ointment or salve for treatment of a variety of skin disorders.

The invention provides compositions of matter comprising a biologically-active compound covalently linked to a polar lipid carrier molecule. Preferred embodiments also comprise a spacer molecule having two linker functional groups, wherein the spacer has a first end and a second end and wherein the lipid is attached to the first end of the spacer through a first linker functional group and the biologically-active compound is attached to the second end of the spacer through a second linker functional group. In preferred embodiments, the biologically-active compound is a drug, most preferably an antiproliferative drug or agent, an antibiotic drug, an antiviral drug, an antineoplastic drug or a corticosteroid. Preferred polar lipids include but are not limited to acyl- and acylated carnitine, sphingosine, ceramide, phosphatidyl choline, phosphatidyl glycerol, phosphatidyl ethanolamine, phosphatidyl inositol, phosphatidyl serine, cardiolipin and phosphatidic acid. Preferred biologically-active compounds include antineoplastic and antiproliferative agents such as methotrexate, corticosteroids, antimycotics, antibiotics and antiviral compounds. Pharmaceutical compositions comprising the drug/polar lipid conjugates of the invention formulated with a medicinal ointment or salve are also provided.

The invention also provides compositions of matter comprising a biologically-active compound covalently linked to a lipid, most preferably a polar lipid, carrier molecule via a spacer molecule wherein the spacer allows the biologically-active compound to act without being released at an intracellular site. In these embodiments of the invention, the first linker functional group attached to the first end of the spacer is characterized as "strong" and the second linker functional group attached to the second end of the spacer is characterized as "weak", with reference to the propensity of the covalent bonds between each end of the spacer molecule to be broken.

In other embodiments of the compositions of matter of the invention, the spacer allows the facilitated hydrolytic release of the biologically-active compound at an intracellular site. Other embodiments of the spacer facilitate the enzymatic release of the biologically-active compound at an intracellular site. In particularly preferred embodiments, the spacer functional group is hydrolyzed by an enzymatic activity found in skin, preferably an esterase and most preferably an esterase having a differential expression and activity profile in different skin layers. In additional preferred embodiments, specific release of biologically-active compounds is achieved by enzymatic or chemical release of the biologically-active compound by intracellular cleavage of a cleavable linker moiety in cells infected by a pathogenic organism or otherwise expressing a disease state (for example, hyperplasia associated with a benign or malignant skin condition) via an enzymatic activity specific for such a pathogenic organism or disease state, or by extracellular cleavage of a cleavable linker moiety via an enzymatic activity specific for a pathogenic organism or disease state.

The invention also provides polar lipid drug conjugates that target dermal, intradermal and infradermal structures in skin for delivery of therapeutic agents for the treatment of skin diseases and disorders. Specifically, the invention provides such conjugates comprising a spacer that allows facilitated hydrolytic or enzymatic release of the biologically-active compound at a dermal, intradermal or infradermal site in skin.

In another embodiment of this aspect of the invention, the spacer molecule is a peptide of formula (amino acid)$_n$, wherein n is an integer between 2 and 25, preferably wherein the peptide comprises a polymer of one or more amino acids.

In other embodiments of the compositions of matter of the invention, the biologically-active compound of the invention has a first functional linker group, and a lipid, most preferably a polar lipid, carrier has a second functional linker group, and the compound is covalently linked directly to the lipid carrier by a chemical bond between the first and second functional linker groups. In preferred embodiments, each of the first and second functional linker groups is a hydroxyl group, a primary or secondary amino group, a phosphate group or substituted derivatives thereof or a carboxylic acid group.

In another aspect of the invention is provided compositions of matter comprising a drug, most preferably an antiproliferative drug, an antineoplastic drug, an antibiotic, an antimycotic, or an antiviral drug, covalently linked to a polar lipid carrier molecule. Preferred embodiments also comprise a spacer molecule having two linker functional groups, wherein the spacer has a first end and a second end and wherein the lipid is attached to the first end of the spacer through a first linker functional group and the drug is attached to the second end of the spacer through a second linker functional group. Preferred embodiments of the invention are provided wherein the drug is an antiproliferative agent, such as methotrexate, an antiviral agent such as an antiherpetic agent, an antibiotic agent such as rifampicin or streptomycin, or an antimycotic such as econazole. Preferred polar lipids include but are not limited to acyl- and acylated carnitine, sphingosine, ceramide, phosphatidyl choline, phosphatidyl glycerol, phosphatidyl ethanolamine, phosphatidyl inositol, phosphatidyl serine, cardiolipin and phosphatidic acid. Pharmaceutical compositions comprising the drug/polar lipid conjugates of the invention formulated with a medicinal ointment or salve are also provided.

The invention also provides compositions of matter comprising an antiproliferative agent, an antineoplastic drug, an antibiotic, an antimycotic, or an antiviral drug, covalently linked to a polar lipid carrier molecule via a spacer molecule, wherein the spacer allows the drug to act without being released at an intracellular site. In these embodiments of the invention, the first linker functional group attached to the first end of the spacer is characterized as "strong" and the second linker functional group attached to the second end of the spacer is characterized as "weak", with reference to the propensity of the covalent bonds between each end of the spacer molecule to be broken.

In other embodiments of the compositions of matter of the invention, the spacer allows the facilitated hydrolytic release of an antiproliferative drug, an antineoplastic drug, an antibiotic, an antimycotic, or an antiviral drug, at an intracellular site. Other embodiments of the spacer facilitate the enzymatic release of the antiproliferative, antineoplastic, antibiotic, antimycotic or antiviral drugs of the invention at an intracellular site. In particularly preferred embodiments, the spacer functional group is hydrolyzed by an enzymatic activity found in skin, preferably an esterase and most preferably an esterase having a differential expression and activity profile in different skin layers. In additional preferred embodiments, specific release of the antiproliferative, antineoplastic, antibiotic, antimycotic or antiviral drugs of the invention is achieved by enzymatic or chemical release of these drugs by intracellular cleavage of a cleavable linker moiety in cells infected by a pathogenic organism or otherwise expressing a disease state (for example, hyperplasia associated with a benign or malignant skin condition) via an enzymatic activity specific for such a pathogenic organism or disease state, or by extracellular cleavage of a cleavable linker moiety via an enzymatic activity specific for a pathogenic organism or disease state.

The invention also provides polar lipid conjugates the antiproliferative, antineoplastic, antibiotic, antimycotic or an antiviral drugs of the invention that target dermal, intradermal and infradermal structures in skin for delivery of therapeutic agents for the treatment of skin diseases and disorders. Specifically, the invention provides such conjugates comprising a spacer that allows facilitated hydrolytic or enzymatic release of the of such antiproliferative, antineoplastic, antibiotic, antimycotic or an antiviral drugs at a dermal, intradermal or infradermal site in skin.

In another embodiment of this aspect of the invention, the spacer molecule is a peptide of formula (amino acid)$_n$, wherein n is an integer between 2 and 25, preferably wherein the peptide comprises a polymer of one or more amino acids.

In still further embodiments of the compositions of matter of the invention are provided an antiproliferative drug, an antineoplastic drug, an antibiotic, an antimycotic, or an antiviral drug, having a first functional linker group, and a polar lipid carrier having a second functional linker group, wherein the drug is covalently linked directly to the polar lipid carrier by a chemical bond between the first and second functional linker groups. In preferred embodiments, each of the first and second functional linker groups is a hydroxyl group, a primary or secondary amino group, a phosphate group or substituted derivatives thereof or a carboxylic acid group. Preferred embodiments of the invention are provided wherein the drug is an antiproliferative agent, such as methotrexate, an antiviral agent such as an antiherpetic agent, an antibiotic agent such as rifampicin or streptomycin, or an antimycotic such as econazole. Preferred polar lipids include but are not limited to acyl- and acylated carnitine, sphingosine, ceramide, phosphatidyl choline, phosphatidyl glycerol, phosphatidyl ethanolamine, phosphatidyl inositol, phosphatidyl serine, cardiolipin and phosphatidic acid. Pharmaceutical compositions comprising the drug/polar lipid conjugates of the invention formulated with a medicinal ointment or salve are also provided.

The invention also provides compositions of matter comprising an antiproliferative drug, an antineoplastic drug, an antibiotic, an antimycotic, or an antiviral drug covalently linked to a polar lipid carrier molecule via a spacer molecule wherein the spacer allows the drug to act without being released at an intracellular site. In these embodiments of the invention, the first linker functional group attached to the first end of the spacer is characterized as "strong" and the second linker functional group attached to the second end of the spacer is characterized as "weak", with reference to the propensity of the covalent bonds between each end of the spacer molecule to be broken.

In other embodiments of the compositions of matter of the invention, the spacer allows the facilitated hydrolytic release of the antiproliferative, antineoplastic, antibiotic, antimycotic or an antiviral drug at an intracellular site. Other embodiments of the spacer facilitate the enzymatic release of a drug as provided by the invention at an intracellular site. In particularly preferred embodiments, the spacer functional group is hydrolyzed by an enzymatic activity found in skin, preferably an esterase and most preferably an esterase having a differential expression and activity profile in different skin layers. In additional preferred embodiments, specific release of the antiproliferative, antineoplastic, antibiotic, antimycotic or antiviral drugs of the invention is achieved by enzymatic or chemical release of these drugs by intracellular cleavage of a cleavable linker moiety in cells infected by a pathogenic organism or otherwise expressing a disease state (for example, hyperplasia associated with a benign or malignant skin condition) via an enzymatic activity specific for such a pathogenic organism or disease state, or by extracellular cleavage of a cleavable linker moiety via an enzymatic activity specific for a pathogenic organism or disease state.

In other embodiments of the compositions of matter of the invention, the spacer allows the facilitated enzymatic or hydrolytic release of the antiproliferative, antineoplastic, antibiotic, antimycotic or an antiviral drug at dermal, intradermal and infradermal structures in skin for delivery of therapeutic agents for the treatment of skin diseases and disorders.

In another embodiment of this aspect of the invention, the spacer molecule is a peptide of formula (amino acid)$_n$, wherein n is an integer between 2 and 25, preferably wherein the peptide comprises a polymer of one or more amino acids.

Preferred embodiments of this aspect of the invention include compositions of matter that are N-methotrexate ceramide, methotrexate-glycylglycylglycylglycylglycyl (SEQ ID No: 1) ceramide ester, methotrexate-(tri-β-hydroxypropionylester)-O$^x$-ceramide ester, methotrexate-glycylglycylglycylglycyl (SEQ ID No: 1) ceramide ester, methotrexate-aminohexanoyl sphingosine amide, methotrexate-valinylvalinyl sphingosine amide and methotrexate-O$^x$-ceramide ester.

Particular preferred embodiments of the polar lipid/drug conjugates of this invention are provided as salves and other topically or locally applied compositions comprising the drug/polar lipid conjugates of the invention and any of a variety of emollients or other commonly encountered components of cremes, salves, poultices, lotions, gels or other substances well-known in the art for applying compounds to skin and other tissues. Appropriate formulations of such compositions comprising the drug/polar lipid conjugates of the invention will be apparent and within the skill of one of ordinary skill in this art to advantageously prepare in view of the instant disclosure.

In preferred embodiments, the drug/lipid conjugates of the invention comprise a functionality recognized by an enzymatic activity, most preferably an esterase activity, that has a differential pattern of expression or activity in different skin layers. In additional preferred embodiments, specific release of the antiproliferative, antineoplastic, antibiotic, antimycotic or antiviral drugs of the invention is achieved by enzymatic or chemical release of these drugs by intracellular cleavage of a cleavable linker moiety in cells infected by a pathogenic organism or otherwise expressing a disease state (for example, hyperplasia associated with a benign or malignant skin condition) via an enzymatic activity specific for such a pathogenic organism or disease state, or by extracellular cleavage of a cleavable linker moiety via an enzymatic activity specific for a pathogenic organism or disease state.

As disclosed herein, the invention comprehends a polar lipid-drug conjugate wherein the polar lipid will selectively associate with certain biological membranes, and thereby facilitate entry of the drug into cells and cellular organelles. In embodiments comprising a spacer moiety, the spacer component of the conjugates of the invention will preferably act to release the drug from the lipid, target the conjugate to the cell, or perform other functions to maximize the effectiveness of the drug.

This type of conjugate has numerous advantages. First, the drug-lipid conjugates of the invention promote the intracellular entry of a variety of potentially useful drugs at pharmokinetic rates not currently attainable. Second, the range of targeted cell types is not limited per se by particular, limited biological properties of the cell (such as the number and type of specific receptor molecules expressed on the cell surface). Third, in contrast to traditional attempts to simply target drugs to specific cells, this method may target drugs to specific intracellular organelles and other intracellular compartments. Fourth, the compositions of matter of the invention incorporate a variable spacer region that may allow pharmacologically-relevant rates of drug release from polar lipid carrier molecules to be engineered into the compositions of the invention, thereby increasing their clinical efficacy and usefulness. Thus, time-dependent drug release and specific drug release in cells expressing the appropriate degradative enzymes are a unique possibility using the drug-lipid conjugates of the invention. Fifth, the conjugates of the invention can be combined with other drug delivery approaches to further increase specificity and to take advantage of useful advances in the art. Sixth, the conjugates of the invention can be topically applied to skin, and the layer of skin penetrated determined by the formulation used. Seventh, in such formulations, the amount and activity of the topically-applied drug can be modulated by release via cleavage, preferably hydrolytic cleavage, of the spacer moiety, most preferably by an enzymatic activity in skin that has a differential pattern of expression or activity in different skin layers.

Specific preferred embodiments of the present invention will become evident from the following more detailed description of certain preferred embodiments and the claims.

DETAILED DESCRIPTION OF THE PREFERRED ENMBODIMENTS

Figure 1:
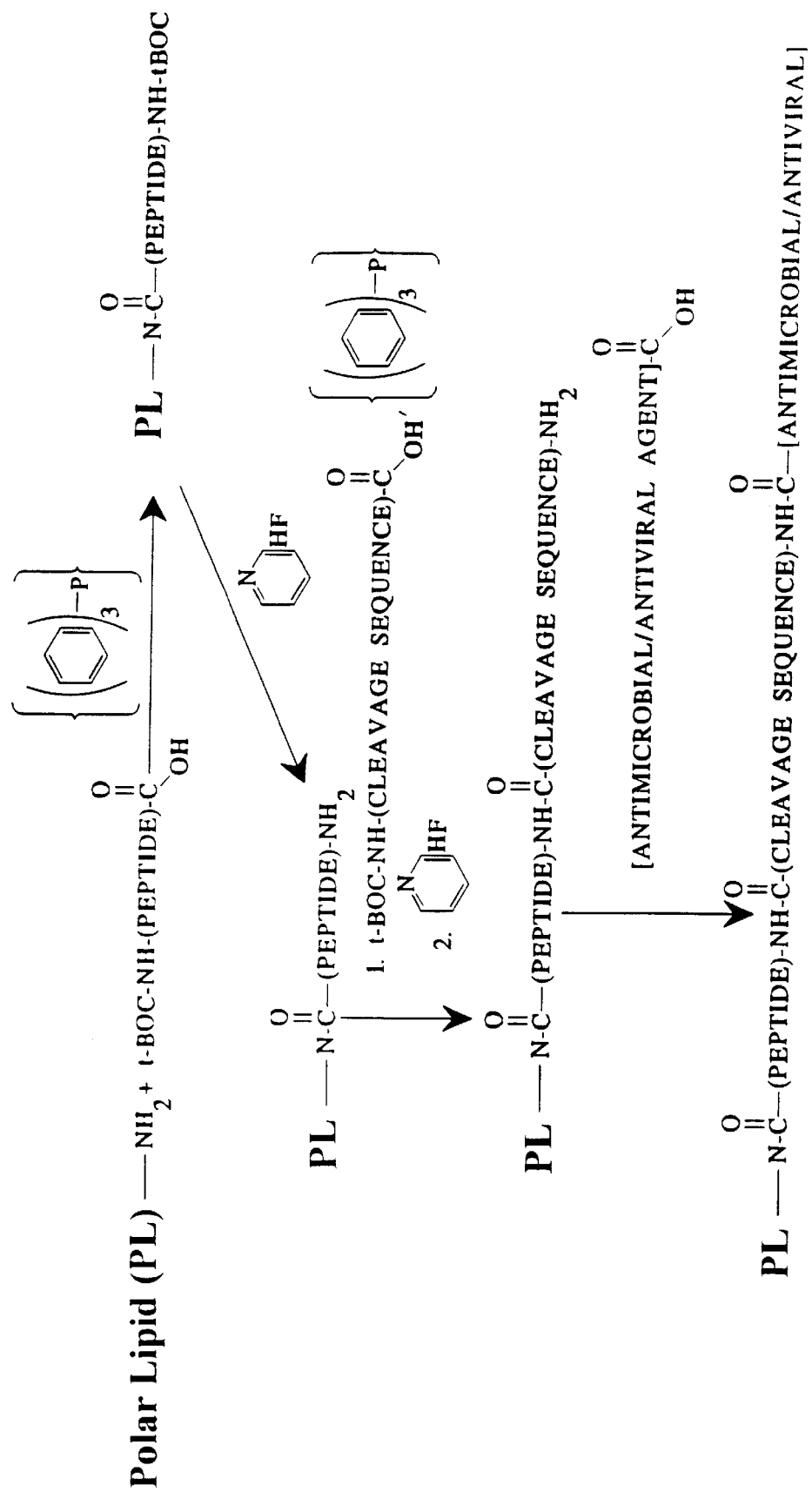
FIG. 1 depicts the synthetic scheme put forth in Example 1.

The present invention provides compositions of matter and methods for facilitating the entry into cells of biologically-active compounds. For the purposes of this invention, the term "biologically-active compound" is intended to encompass all naturally-occurring or synthetic compounds capable of eliciting a biological response or having an effect, either beneficial or cytotoxic, on biological systems, particularly cells and cellular organelles. These compounds are intended to include but are not limited to all varieties of drugs, particularly antiproliferative drugs and agents, antibacterial, fungicidal, anti-protozoal and antiviral drugs, antineoplastic drugs, and cytotoxic and cytostatic compounds.

Pharmaceutical compositions comprising the drug/polar lipid conjugates of the invention formulated with a medicinal ointment or salve are also provided. As used herein the terms "medicinal ointment or salves" are considered equivalent. The term is intended to encompass any of a variety of salves and other topically or locally applied formulations known in the art, and specifically to encompass any of a variety of emollients or other commonly encountered components of cremes, salves, poultices, lotions, gels or other substances well-known in the art for applying compounds to skin and other tissues. Appropriate formulations of such compositions comprising the drug/polar lipid conjugates of the invention will be apparent and within the skill of one of ordinary skill in this art to advantageously prepare in view of the instant disclosure.

The compositions of matter provided by the invention comprise the biologically-active compounds of the invention covalently linked to a polar lipid carrier. A polar lipid carrier, as defined herein is intended to mean any polar lipid having an affinity for, or capable of crossing, a biological membrane, including but not limited to sphingosine, ceramide, phosphatidyl choline, phosphatidyl glycerol, phosphatidyl ethanolamine, phosphatidyl inositol, phosphatidyl serine, cardiolipin, phosphatidic acid, sphingomyelin and other sphingolipids, as these terms are understood in the art (see, Lehninger, *Biochemistry*, 2d ed., Chapters 11 & 24, Worth Publishers: New York, 1975). Additionally, certain other lipids, such as acylated carnitine, comprise the conjugates of the invention (see Small, 1986, "From alkanes to phospholipids," *Handbook of Lipid Research: Physical Chemistry of Lipids*, Volume 4, Chapters 4 and 12, Plenum Press: New York).

The compositions of matter of the invention may be further comprised of a spacer moiety comprising a first end and a second end, each end of the spacer having a functional linking group. For the purposes of this invention, the term "spacer" or "spacer moiety" is intended to encompass any chemical entity that links the biologically-active compound and the polar lipid. Such spacer moieties may be designed to facilitate the attachment of the conjugates of the invention to a target cell, or to facilitate, influence, modulate or regulate the release of the biologically-active compound at the desired target site. Such spacers may also facilitate enzymatic release at certain intracellular sites. Spacer groups, as described herein, include, but are not limited to aminohexanoic acid, polyglycine, polyamides, polyethylenes, and short functionalized polymers having a carbon backbone which is from one to about twelve carbon molecules in length. Particularly preferred embodiments of such spacer moieties comprise peptides of formula (amino acid)$_n$, wherein n is an integer between 2 and 25 and the peptide is a polymer of one or more amino acids.

The term "linker functional group" is defined herein as any functional group for covalently binding the polar lipid carrier or biologically-active agent to the spacer group. These groups can be designated either "weak" or "strong" based on the stability of the covalent bond which the linker functional group will form between the spacer and either the polar lipid carrier or the biologically-active compound. The weak functionalities include, but are not limited to phosphoramide, phosphoester, carbonate, amide, carboxyl-phosphoryl anhydride, ester and thioester. The strong functionalities include, but are not limited to ether, thioether, amine, amide and ester. The use of a strong linker functional group between the spacer group and the biologically-active compound will tend to decrease the rate at which the compound will be released at the target site, whereas the use of a weak linker functional group between the spacer group and the compound may act to facilitate release of the compound at the target site. Enzymatic release is, of course, also possible, but such enzyme-mediated modes of release will not necessarily be correlated with bond strength in such embodiments of the invention. Spacer moieties comprising enzyme active site recognition groups, such as spacer groups comprising peptides having proteolytic cleavage sites therein, are envisioned as being within the scope of the present invention.

The drug/polar lipid conjugates of the invention are preferably provided comprised of spacer moieties that impart differential release properties on the conjugates related to differential expression or activity of enzymatic activities in different layers of skin. Biologically active agents such as antiproliferative, antiviral or antineoplastic drugs linked to polar lipids can be delivered to different layers and structures in the skin based on the distinct differences in lipid handling within the skin. Such different structures include dermal, intradermal and infradermal regions or sections of the skin. As shown herein in Example 11, there are important differences in the delivery of a fluorescent marker in mouse skin, based on the polar lipid to which it was linked via an amide bond. In addition to distribution by lipid handling, differences in hydrolytic enzymes activity, such as esterases and peptidases, within the skin may be employed to convey specificity to drug distribution.

For example, hydrolysis of esters within the skin by native esterases has been well documented. Moreover, the unique pattern of metabolites found herein suggested that skin expresses a collection of esterases different than other high esterases containing organs, such as liver (Henrikus and Kampffmeyer, 1992, *Xenobiotica* 22: 1357–1366). Significant variation in substrate specificity among esterases has been shown previously. For example, Heymann et al (1993, *Chem. Biol. Interactions* 87: 217–226) showed the existence of at least three families of β-type esterase, identified by pI and all of which had activity with simple aromatic and aliphatic esters. The rate of ester hydrolysis within skin has been found to be significant. Boehnlein et al. (1994, *Pharmaceutical Research* 11:1155–1159) showed that about half of dermally-applied retinyl palmitate was hydrolyzed within a few minutes; similar results were reported with methyl salicylate. β-methasone-17-valerate, a steroid fatty acid ester, has also been reported to be hydrolyzed at a pharmacologically-important rate by skin esterases (Kubota et al., 1994, *Dermatology* 188:13–17). In addition, smaller molecules are delivered more efficiently to skin linkage with lipids. For example, Buyuktimkin el al. (1993, *Pharmaceutical Research* 10:1632–1637) found that uptake of indomethacin and clonidine could be enhanced by linkage to a polar lipid.

Distribution of specific esterases within the skin has not been extensively studied. It is known that some cell types do possesses different constituent esterases. The Langerhans cells contain an α-naphthylacetate hydrolyzine esterase, used in antigen recognition and processing, that is not found in other cell types (Lipozencic et al., 1994, *Eur. J. Histochem.* 38:303–310). Ketatinocytes are also known to have high levels of chloroacetate esterase (Katz et al., 1995, *Brit. J. Dermatology* 133: 842–846).

Esterase activity is also known to vary with pathological conditions. Nonspecific esterase activity increases in cells around the edge of many types of wounds (Dachun et al., 1992, *Forensic Science International* 53: 203–213). Although not produced by skin cells per se, esterases are known to increase in the skin due to influx of other cell types during illness. On example is chloroacetate esterase activity is increased in any condition causing chronic uticaria due to mast cell infiltration (Barlow et al., 1995, *Clinical & Experimental Allergy* 25: 317–322). In another example, monocytes and macrophages found in the skin in leprosy increase esterase activity (SivaSai et al., 1993, *Int. J. Leprosy & Other Mycobacterial Diseases* 61: 259–269).

Other enzymatic activities are associated with skin. Peptidases are found in high levels within skin tissues and the non-dermal cell types infiltrating the skin. Expression of both endo- and exo-peptidases and proteases varies with cell type and pathological condition. Skin fibroblasts contain high levels of peptidases, not seen in other more highly differentiated layers of skin (Bou-Gharios et al., 1995, *Annals of Rheumatic Disease* 54: 111–116). High levels of dipeptidyl dipeptidase IV are seen in precancerous dermatoses and basal cell carcinoma (Moehrle et al., 1995, *J. Cutaneous Pathology* 22: 241–247). Increased peptidase activity is associated with stress responses: exemplary are apoptotic skin cells produced after UV irradiation (so-called sunburn cells), which have high amino and endopeptidase activity: Brown et al. (1994, *J. Cellular Biochemistry* 54: 320–331) have suggested that these apoptotic keratinocytes may be essential elements in the repair process for epithelial cells.

The current state of knowledge of these hydrolytic enzymes in skin is not extensive relative to other organs. However, sufficient data is available to see that there are differences in substrate specificity and enzyme activity that can be exploited to further refine the specificity of the polar lipid delivery vehicle. Formulation of cleavable linkages directed at these enzymes, combined with the larger distributive properties of the lipid carries could provide important new ways to deliver pharmaceutical agents to highly defined locations in the skin, dependent on either normal skin or pathological conditions. Conjugates that advantageously utilize the differential expression and/or activity levels of esterases, proteases, and other enzymatic functionalities are provided by this invention.

As provided by this invention, the specificity of the cleavage of the linker moiety as provided by this invention is the result of the combination of particular linker moieties selected to be specifically cleaved inside an infected skin cell. In one aspect, such specific cleavage is due to an chemical linkage which is labile within the infected cell due to conditions caused by or that result from infection of the cell with a particular pathogenic organism. In another aspect, such specific cleavage is due to an enzymatic activity which is produced either by the pathogen itself or by the cell as the result of infection with said pathogen, wherein the linkage is enzymatically cleaved by the enzymatic activity. Similarly, specific cleavage is obtained in cells expressing a disease or pathologic state, whereby a chemical linkage labile to the conditions inside the diseased cell or enzymatic cleavage due to an enzymatic activity expressed in a diseased cell using drug/polar lipid conjugates comprising the appropriate linking moiety comprising the labile chemical linkage or enzyme recognition site. Differences in skin and other tissues present extracellularly due to the expression of a disease state or the presence of a pathogenic organism are also comprehended to be within the scope of the invention.

Examples of such combinations resulting in specific release of an antimicrobial drug embodiment of the invention within infected cells include but are not limited to a urea-based linker for use against a pathogen which produces urease (e.g., Mycobacteria spp. and *B. pertussis*); a peptide linker comprised of $(AlaAlaAlaAla)_n$(SEQ ID No: 2), wherein n can be an integer from 1–5, for use against a pathogen that produces the protease oligopeptidase A (e.g., Salmonella spp.); a peptide comprised of from 3 to about 20 amino acids comprising the sequence-Pro-Xaa-Pro-, where Xaa is any amino acid, for use against a pathogen that produces proline peptidase (e.g., Salmonella spp.); peptides comprising the dipeptide MetMet or LeuAla, or peptides comprising the amino acid sequence GSHLVEAL (SEQ ID No: 3), HLVRALYL (SEQ ID No: 4), VEALYLVC (SEQ ID No: 5), or EALYLVCG (SEQ ID No: 6), for use against human immunodeficiency virus 1 producing a specific protease termed HIV-1 protease; a peptide comprising the amino acid sequence: -Ala-Xaa-$Cys_{Acm}$-Tyr-Cys-Arg-Ile-Pro-Ala-$Cys_{Acm}$-Ile-Ala-Gly-Asp-Arg-Arg-Tyr-Gly-Thr- Cys$_{Acm}$-Ile-Tyr-Gln-Gly-Arg-Leu-Trp-Ala-Phe-Cys$_{Acm}$-Cys$_{Acm}$-(SEQ ID No: 7), wherein the pathogen expresses an enzymatic activity that specifically disables the endogenous antimicrobial peptide defensin (e.g., Mycobacterium spp. and L. pneumophila), (-Cys$_{Acm}$-) represents cysteine residues having the sidechain sulfur atom protected by covalent linkage to an acetamidomethyl group (it will be recognized that embodiments of such peptides having alternative sulfur protecting groups are also within the scope of the disclosure herein) and Xaa is either absent or Asp (said peptides are also useful against a pathogen such as Legionella spp. producing a 39 kDa metalloprotease); hippurate esters that are hydrolyzed by pathogen-specific (e.g., L. pneumophila and Listeria spp.) hydrolase; nicotinic acid amides cleaved by nicotinamidases, pyrazinamides cleaved by pyrazinamidase; allolactose linkages cleaved by β-galactosidase; and allantoate linkages cleaved by allantoicase (e.g., Mycobacterium spp.).

Thus, the present invention provides methods and compositions of matter for facilitating the entry of antiproliferative, antibiotic, antimycotic, antiviral and antineoplastic agents, drugs and compounds into dermal and epidermal cells, across mucosal membranes where appropriate, and distributed within skin tissue for efficient delivery of such compounds locally and topically for the treatment of animal, preferably human, diseases and pathological conditions. The invention provides salves, ointments, poultices and other topically-applied embodiments of the drug/lipid conjugates of the invention for the treatment of a variety of skin diseases and disorders.

Among the most common dermatological complaints is dermatitis, further differentiated into contact, seborrheic, nummular, exfoliative stasis, and neurodermatitis. Vesicular dermatitis, commonly referred to as eczema, is separated from other dermatitis to reflect the chronic nature of the condition. All forms of dermatitis are characterized by superficial inflammation, vesiculation and localized edema. Accompanying these psoriasiform conditions is thickening of the epidermis showing both hyperkeratosis and parakeratosis. Topical corticosteroids are widely prescribed for these conditions, including the Potency class I drugs betamethasone dipropionate, clobetasol propionate, diflorasone diacetate and flucinolone. Of particular interest in the treatment of psoriasis is methotrexate, the use of which is severely limited by the nephro- and hepatotoxicity. In a preferred embodiment, the invention provides a conjugate, methotrexate ceramide ester (ME6C), that does not concentrate in either liver or kidney to the same extent as the free drug, and is therefore useful in for treatment of chronic psoriasis and related conditions.

Another skin condition conventionally treated by topical application of an antineoplastic agent is the treatment of precancerous lesions classified as actinic keratoses. These lesions respond to 5-fluorouracil (5-FU) topically applied in a propylene glycol carrier. However, topical application of 5-FU is limited by the toxicity of this compound in the systemic circulation. Topical application can be improved by covalent, hydrolyzable linkage of 5-FU to polar lipids that is cleaved by an esterase or peptidase activity in skin. Such compounds have the advantage of better penetration, longer retention and controlled release of active drug.

Superficial fungal infections by the genera Microsporum, Trichophyton, and Epidermophyton, the so-called dermatophyte infections, are extremely common. Ringworm and the Tenia infections, including candidiasis, colonize the area between the dead skin and living layers eliciting vesicular and bullous diseases as well as inflamed lesions of the scalp due to strong immunological responses to the fungi. All respond, to some extent, to topical antifungals. Topical application reduces reliance on systemic antifungals, avoiding the hepatic toxicity produced by administration of the currently used antifungals such as ketoconazole, grisefulvin, ciclopixox, naftitine and other imidizole antimycotics. By conjugating these compounds with polar lipid carriers, these drugs are delivered to specific areas of the skin in greater quantity and maintained for longer periods of time as a consequence of the lipid formulation. Release of active drug from these reservoirs is effectuated by the cleavage of hydrolyzable bonds between the drug and the lipid carrier. By relying on the specific partitioning effect of the polar lipids, a greater therapeutic index is thereby achieved, thus reducing the need for system antimycotics and reducing the risk of hepatic toxicity. In addition, the characteristic accumulation of fluids in eczema, or other bullus conditions, may be a limiting factor in the delivery of water soluble antimycotics. Use of the lipid prodrugs to effectively deliver antifungals to deeper skin structures would improve treatment of eczema and yeast-exacerbated dermatitis.

In skin infestations and dermatitis, deep colonization or involvement of sub-epidermal structures is common. Delivery of drugs to deep skin structures is important for relief of these conditions. The conjugation of compounds to polar lipids, as shown in Example 10 below, indicates that transport and release of medicaments through the skin is possible.

The invention provides polar lipid/drug conjugates comprising corticosteroids, including but not limited to cortisone, cortisol, hydrocortisone, prednisone, fluorinated corticosteroids (such as fluocinalone and triamcinolone), dexamethasone, alcloethasone, fluoroandrenolide and mometasone.

The invention provides polar lipid/drug conjugates comprising antimycotic compounds including but not limited to clotrimazole, ciclopirox, nystatin, econazole and myconixole. The invention provides polar lipid/drug conjugates comprising antibiotics including but not limited to penicillin and drugs of the penicillin family of antimicrobial drugs, including but not limited to penicillin-G, penicillin-V, phenethicillin, ampicillin, amoxacillin, cyclacillin, bacampicillin, hetacillin, cloxacillin, dicloxacillin, methicillin, nafcillin, oxacillin, azlocillin, carbenicillin, mezlocillin, piperacillin, ticaricillin, and imipenim; cephalosporin and drugs of the cephalosporin family, including but not limited to cefadroxil, cefazolin, caphalexn, cephalothin, cephapirin, cephradine, cefaclor, cefamandole, cefonicid, cefoxin, cefuroxime, ceforanide, cefotetan, cefmetazole, cefoperazone, cefotaxime, ceftizoxime, ceftizone, moxalactam, ceftazidime, and cefixime; aminoglycoside drugs and drugs of the aminoglycoside family, including but not limited to streptomycin, neomycin, kanamycin, gentamycin, tobramycin, amikacin, and netilmicin; macrolide and drugs of the macrolide family, exemplified by azithromycin, clarithromycin, roxithromycin, erythromycin, lincomycin, and clindamycin; tetracyclin and drugs of the tetracyclin family, for example, tetracyclin, oxytetracyclin, democlocyclin, methacyclin, doxycyclin, and minocyclin; quinoline and quinoline-like drugs, such as, for example, naladixic acid, cinoxacin, norfloxacin, ciprofloxacin, ofloxicin, enoxacin, and pefloxacin; antimicrobial peptides, including but not limited to polymixin B, colistin, and bacatracin, as well as other antimicrobial peptides such as defensins (Lehrer et al., 1991, Cell 64: 229–230), magainins (Zasloff, 1987, Proc. Natl. Acad. Sci. USA 84: 5449–5453), cecropins (Lee et al., 1989, Proc. Natl. Acad. Sci. USA 86:9159–9162 and Boman et al., 1990, Eur.

J. Biochem. 201: 23–31), and others, provided as naturally-occurring or as the result of engineering to make such peptides resistant to the action of deactivating enzymes; other antibiotic drugs, including chloramphenicol, vancomycin, rifampicin, metronidazole, ethambutol, pyrazinamide, sulfonamides, isoniazid, and erythromycin.

The invention also provides polar lipid/drug conjugates of antiviral agents, including but not limited to reverse transcriptase inhibitors, protease inhibitors, antiherpetics such as acyclovir and gangcyclovir, azidothymidine, cytidine arabinoside, ribavirin, amantadine, iododeoxyuridine, poscarnet, trifluoridine, methizazone, vidarabine and levanisole.

The invention provides polar lipid/drug conjugates of antiproliferative and antineoplastic agents, including but not limited to methotrexate, doxarubicin, daunarubicin, actinomycin D, vinblastine, vincristine, colchicine and taxol.

The invention specifically provides methods for preparing and administering such antiproliferative compounds for use in treating pathological conditions in vivo.

Animals to be treated with polar lipid-antiproliferative agent conjugates using the methods of the invention are intended to include all vertebrate animals, preferably domesticated animals, such as cattle, horses, goats, sheep, fowl, fish, household pets, and others, as well as wild animals, and most preferably humans.

The following Examples illustrate certain aspects of the above-described method and advantageous results. The following examples are shown by way of illustration and not by way of limitation.

EXAMPLE 1

An antibiotic drug/polar lipid conjugate of the invention is prepared by conjugating a specifically-cleavable peptide to a polar lipid and an antibiotic drug as follows. An derivatized polar lipid comprising unconjugated amino groups is reacted with a proteolytically-inert peptide in which the terminal amine and any of the constituent amino acid sidechain reactive amines are covered by tertbutoxy-carbonyl (t-Boc) protecting groups in the presence of triphenyl phosphine as described by Kishimoto (1975, Chem. Phys. Lipids 15:33–36). The peptide/polar lipid conjugate is then reacted in the presence of pyridine hydrofluoride as described by Matsuura et al. (1976, J. Chem. Soc. Chem. Comm. xx:451–459) to remove the t-Boc protecting groups. The peptide/polar lipid is then conjugated to the specifically-cleavable peptide, in which the terminal amine and any of the constituent amino acid sidechain reactive amines are covered by t-Boc protecting groups, as described in the presence of triphenyl phosphine. After deprotection of reactive amines with pyridine hydrofluoride as described, an antibiotic drug having a reactive carboxylic acid group is conjugated to a free amino group of the polar lipid/peptide/ specifically-cleavable peptide to yield the antibiotic drug/ polar lipid conjugate of the invention. This reaction scheme is illustrated in FIG. 1.

EXAMPLE 2

Figure 2:
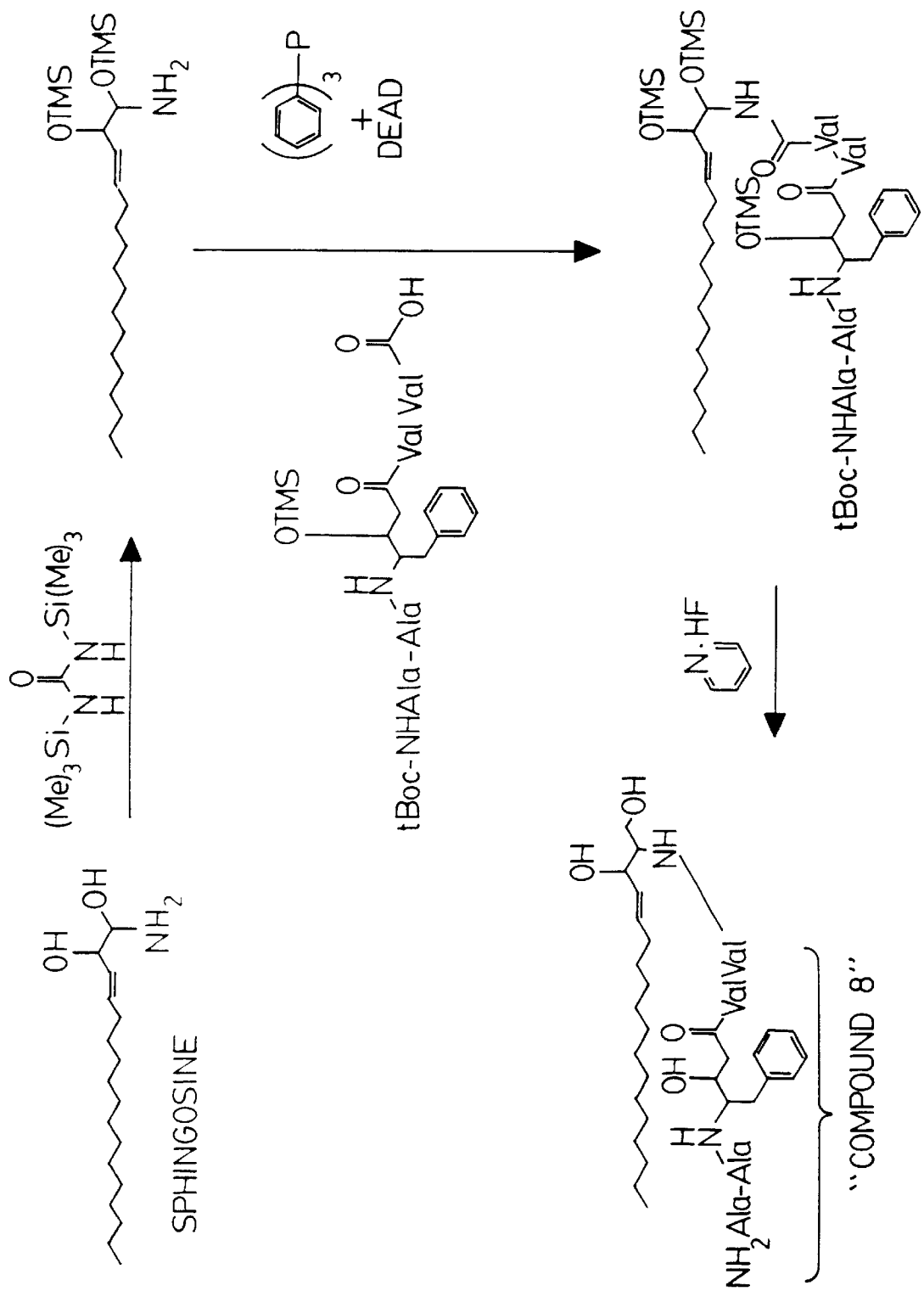
FIG. 2 depicts the synthetic scheme put forth in Example 2.

An antiviral compound (HIV1 protease inhibitor; compound 8) is conjugated to sphingosine as follows. Sphingosine is reacted with 1,3 bis(trimethylsilyl)urea as described by Verbloom et al. (1981, Synthesis 1032:807–809) to give a trimethylsilyl derivative of sphingosine. The sphingosine derivative is then conjugated with a specifically-cleavable peptide in which the terminal amine and any of the constituent amino acid sidechain reactive amines are covered by tert-butoxycarbonyl (t-Boc) protecting groups in the presence of diethylazo-dicarboxylate (DEAD) and triphenyl phosphine as described by Kishimoto (1975, Chem. Phys. Lipids 15: 33–36). The sphingosine/ peptide conjugate is then reacted in the presence of pyridine hydrofluoride as described by Matsuura et al. (1976, J. Chem. Soc. Chem. Comm. xx: 451–459) to remove the t-Boc protecting group, to yield the peptide covalently linked to sphingosine through an amide bond. This reaction scheme is illustrated in FIG. 2. Sphingosine/peptide conjugates are then linked to the antiviral compound as described in Example 1.

EXAMPLE 3

Figure 3:
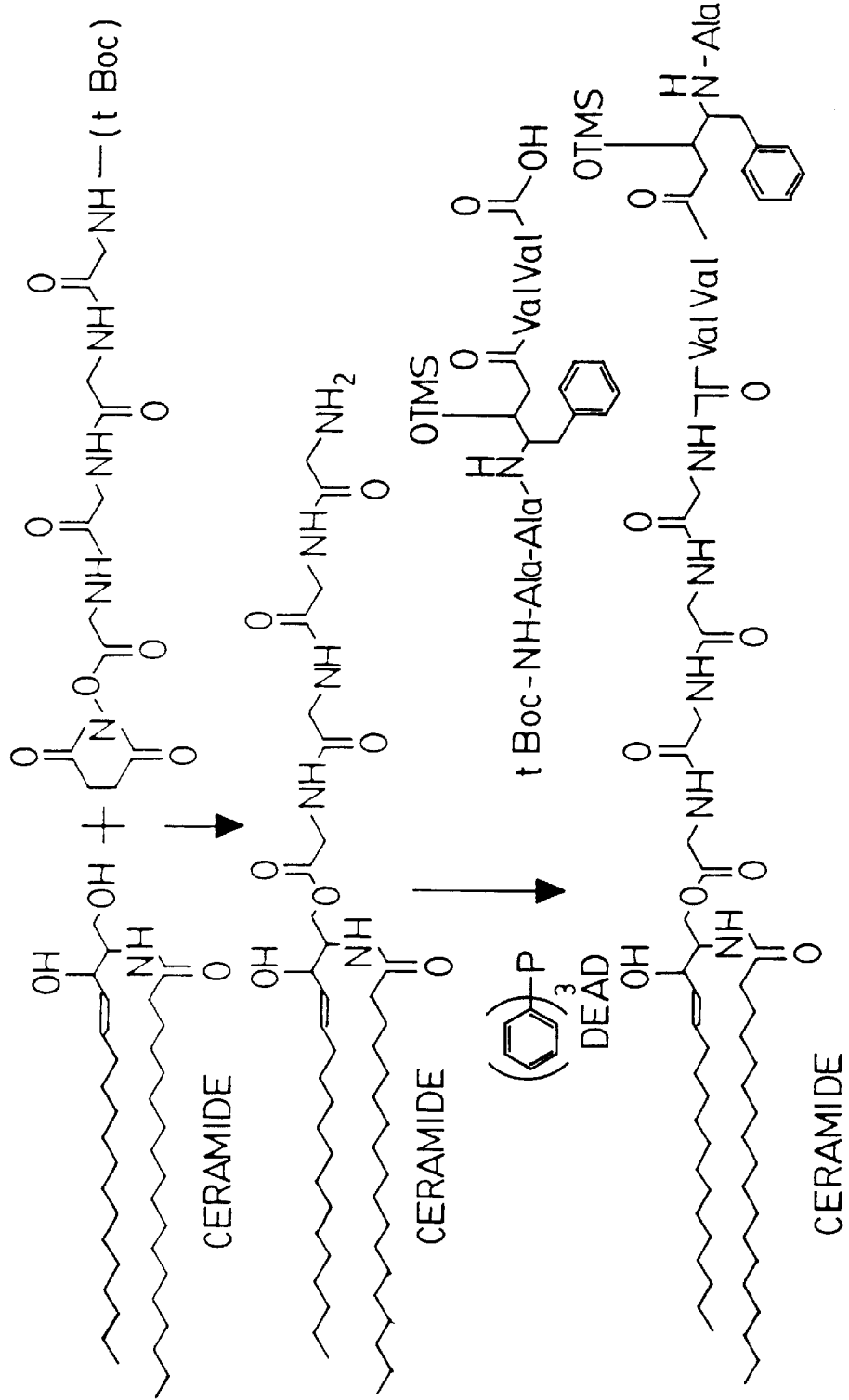
FIG. 3 depicts the synthetic scheme put forth in Example 3.
Figure 3:
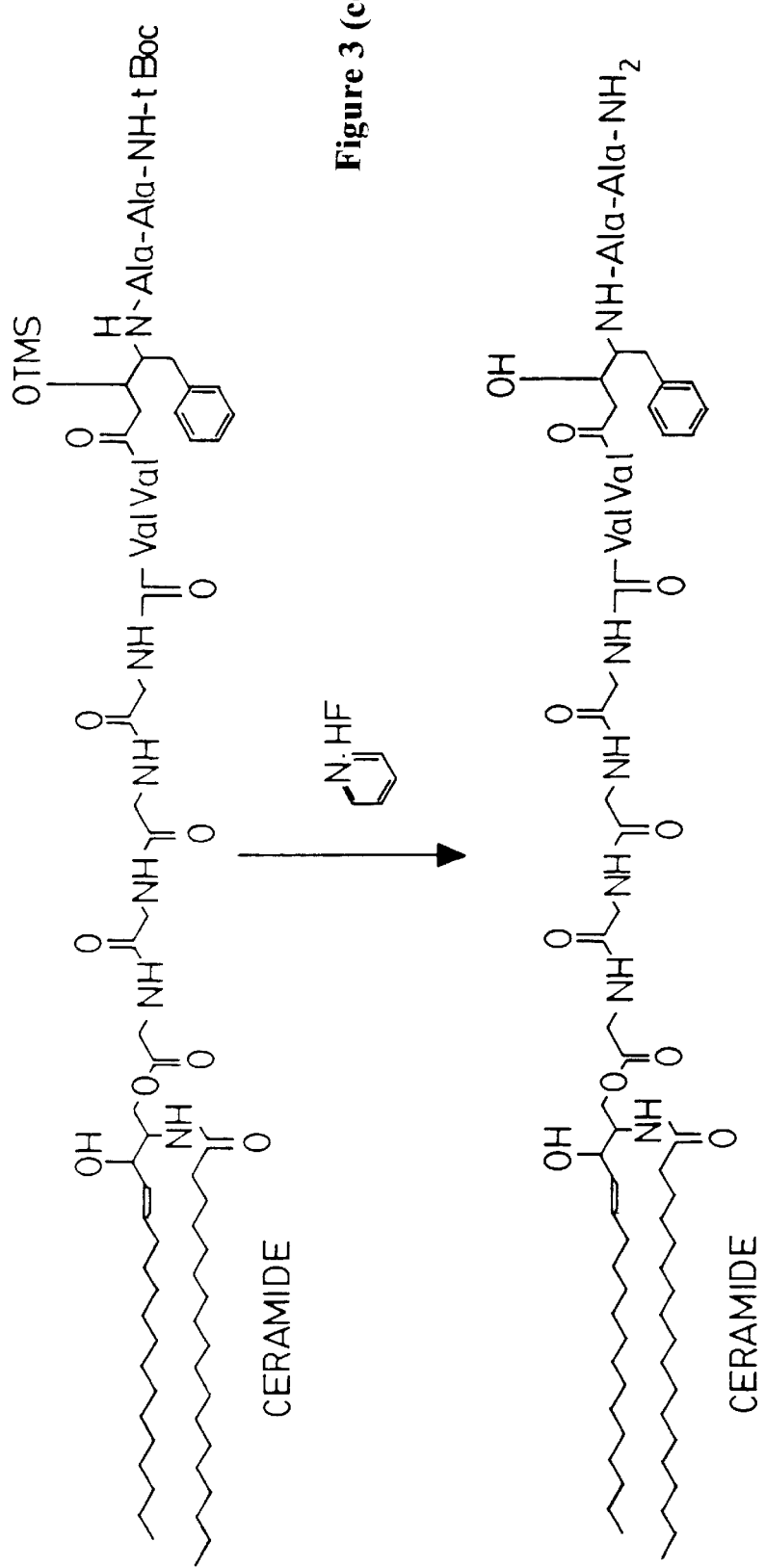

An antiviral compound (compound 8) is conjugated to ceramide via a polyglycine spacer as follows and as illustrated in FIG. 3. The amino terminus of polyglycine is protected by a t-Boc group. Polyglycine is conjugated through its carboxy terminus to ceramide forming an ester linkage, as described in Anderson et al., ibid. The resulting compound is then conjugated through the amino terminus of the polyglycine residue. The amino terminus of Compound 8 is also protected by a t-Boc protecting group. Conjugation with polyglycyl-sphingosine takes place between the amino terminus of the polyglycyl spacer moiety and the carboxy terminus of the HIV-1 protease inhibitor. This reaction is carried out in the presence of DEAD and triphenyl phosphine as described in Examples 1 and 2. Following this conjugation, the amino terminus of the HIV-1 protease inhibitor residue is deprotected according to the method of Matsuura et al., ibid.

EXAMPLE 4

Figure 4:
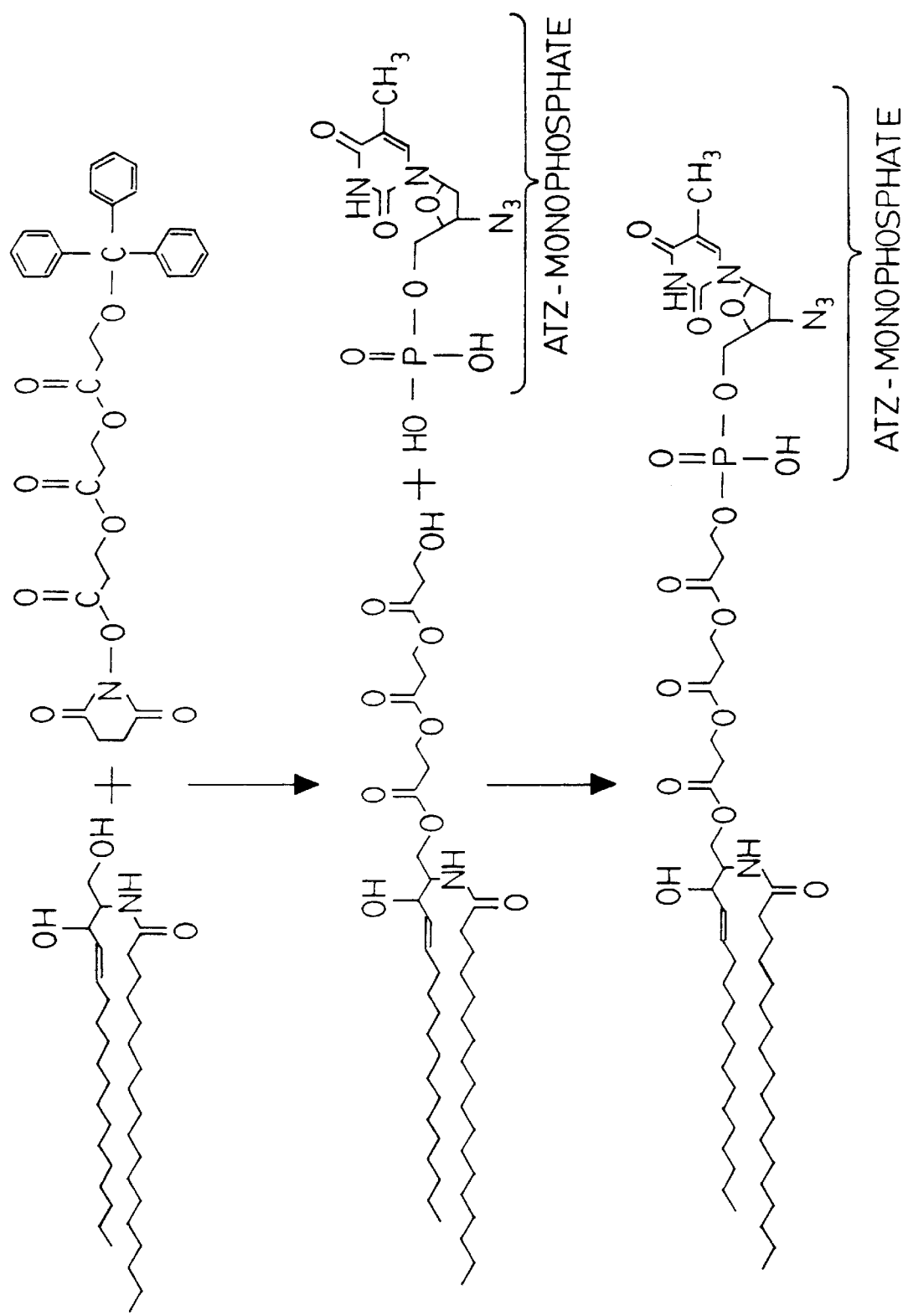
FIG. 4 depicts the synthetic scheme put forth in Example 4.

An antiviral compound is prepared wherein ceramide is first conjugated to a first end of an oligomeric 3-hydroxy propanoic acid spacer through an ester functional group, and wherein AZT is conjugated to a second end of said polyester spacer through a phosphodiester bond. First a polyester spacer is obtained, having a carboxyl at a first end and a triphenylmethyl group esterified to a second end. This spacer is conjugated to ceramide at its first end through an ester functional linker group according to the method of Anderson et al., ibid. This compound is then conjugated through the second end of the spacer compound to AZT monophosphate by means of a phosphodiester bond according to the method of Baer (1955, Can. J. Biochem. Phys. 34: 288). In this antiviral compound, the bond breakage between the spacer and the drug would be slow in the absence of a phosphohydrolase. This reaction scheme is illustrated in FIG. 4.

EXAMPLE 5

Figure 5:
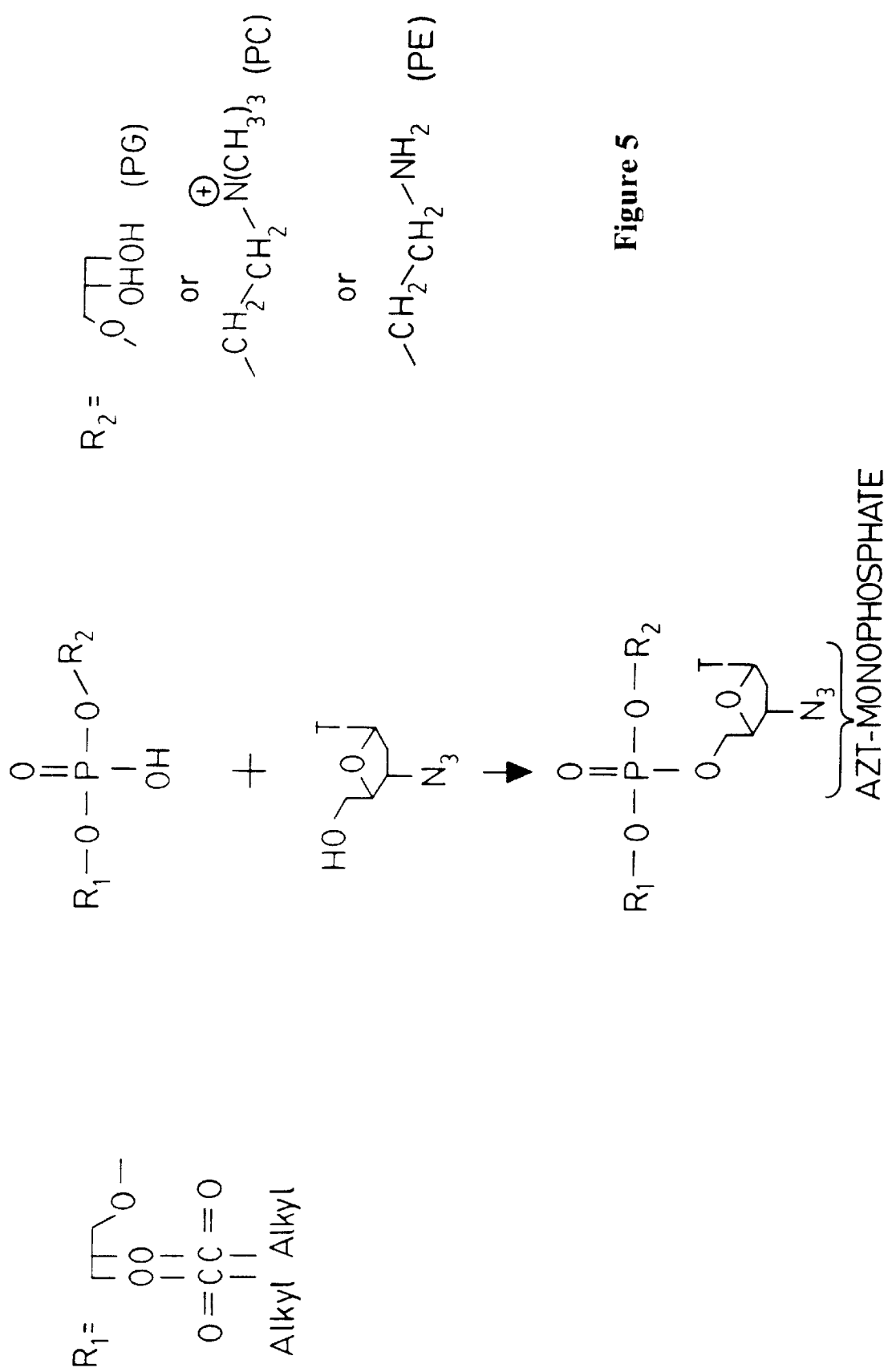
FIG. 5 depicts the synthetic scheme put forth in Example 5.

An antiviral compound wherein phosphatidic acid, phosphatidyl choline, phosphatidyl serine, phosphatidyl inositol, phosphatidyl glycerol or phosphatidylethanolamine is linked through a phosphoester linker functional group to the antiviral drug azidothymidine (AZT). Phosphatidic acid, phosphatidyl choline, phosphatidyl serine, phosphatidyl inositol, phosphatidyl glycerol or phosphatidyl ethanolamine is conjugated to AZT according to the method of Salord et al. (1986, Biochim. Biophys. Acta 886: 64–75). This reaction scheme is illustrated in FIG. 5.

EXAMPLE 6

Figure 6:
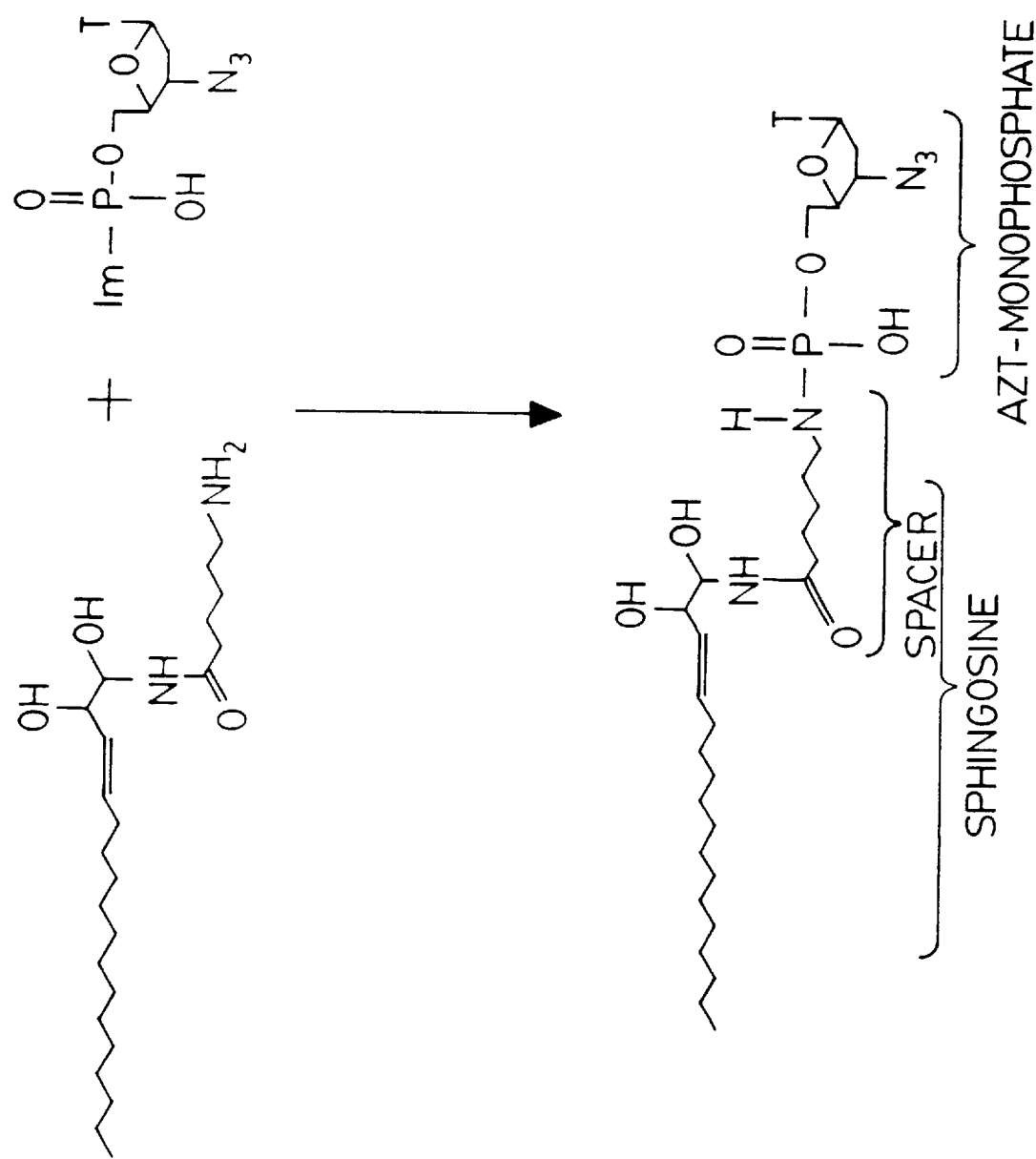
FIG. 6 depicts the synthetic scheme put forth in Example 6.

An antiviral compound is prepared wherein aminohexanoyl sphingosine is conjugated to AZT. Aminohexanoyl sphingosine is conjugated with AZT according to the method of Kishimoto (1975, *Chem. Phys. Lipid* 15: 33–36). This reaction scheme is illustrated in FIG. 6 to yield aminohexanoyl sphingosine conjugated to AZT through a phosphoramide bond.

EXAMPLE 7

Figure 7:
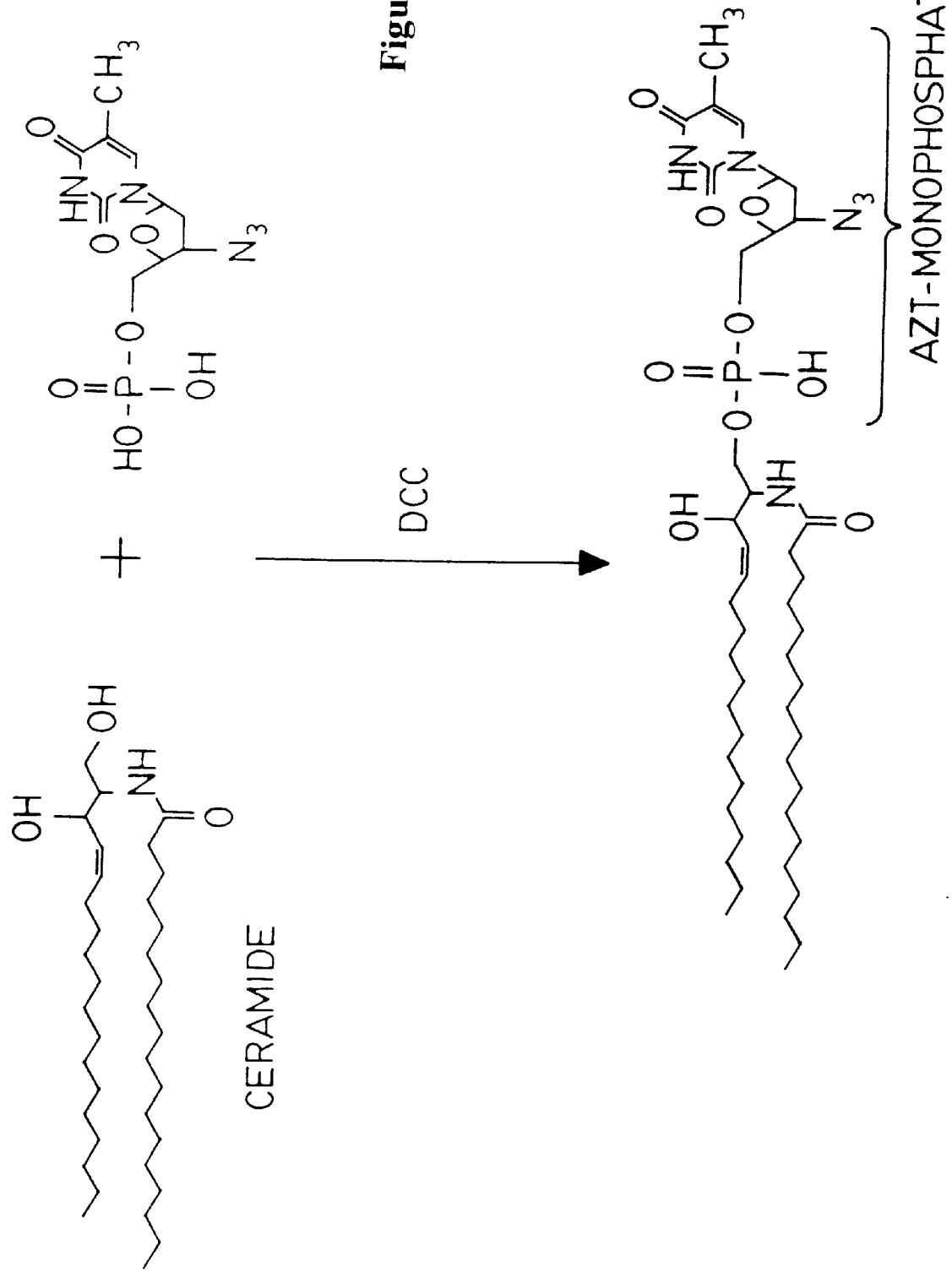
FIG. 7 depicts the synthetic scheme put forth in Example 7.

An antiviral compound consisting of ceramide conjugated to AZT-monophosphate is provided. Ceramide is reacted with AZT-monophosphate in the presence of dicyclohexylcarbodiimide as described in Smith and Khorana (1958, *J. Amer. Chem. Soc.* 80: 1141) to yield ceramide conjugated through a phosphodiester bond to AZT-monophosphate. This reaction scheme is illustrated in FIG. 7.

EXAMPLE 8

Figure 8:
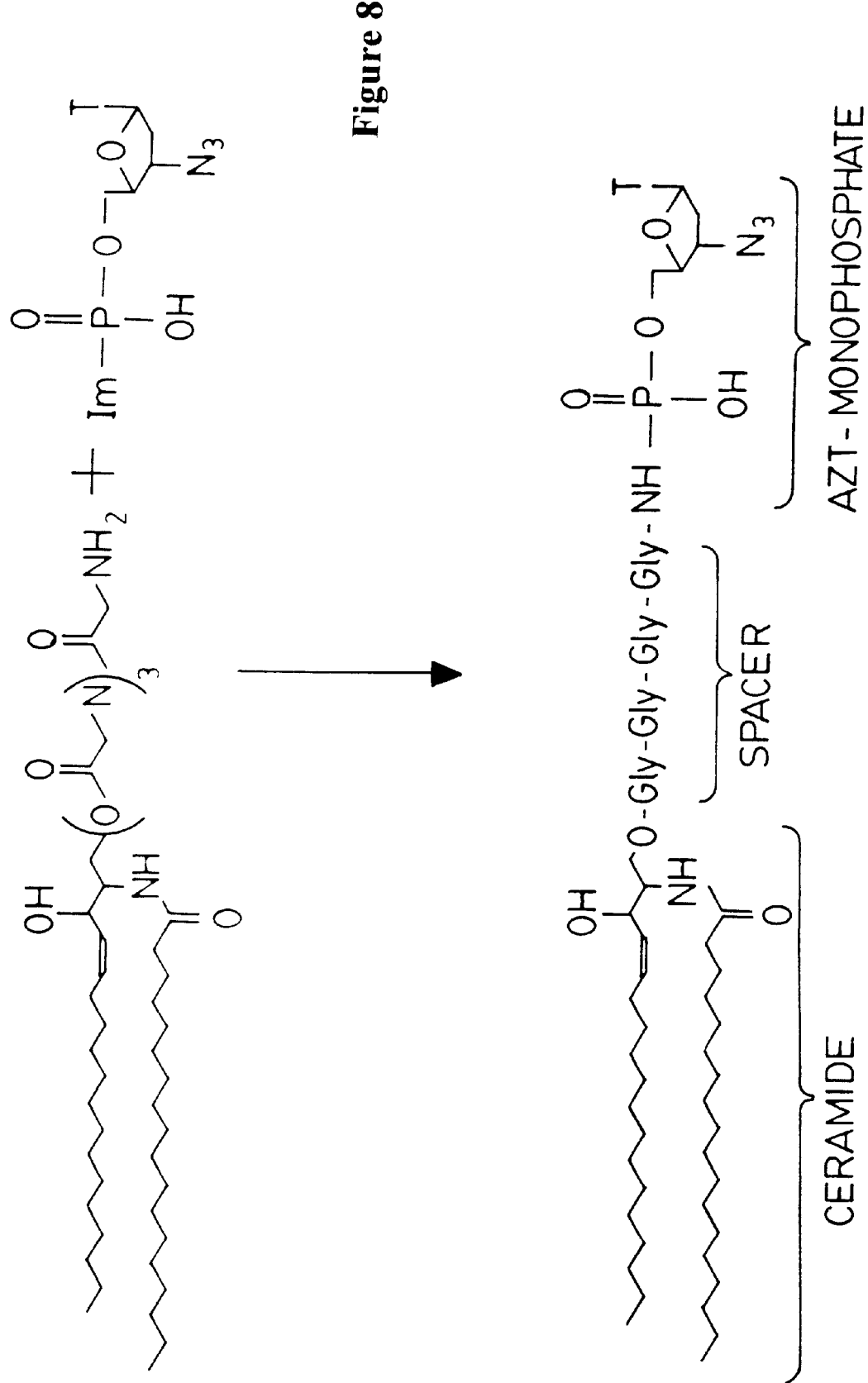
FIG. 8 depicts the synthetic scheme put forth in Example 8.

An antiviral compound is prepared wherein ceramide is conjugated through an ester functional group to a first end of a polyglycine spacer, and wherein AZT is conjugated through a phosphoester functional group to a second end of the polyglycine spacer. Ceramide is first conjugated through an ester functional group to a first end of a polyglycine spacer (as described in Example 2). The ceramide-polyglycine compound is then conjugated through a phosphoester bond to a second end of the polyglycine spacer to AZT monophosphate according to the method of Paul and Anderson, ibid. This reaction scheme is illustrated in FIG. 8.

EXAMPLE 9

Figure 9A:
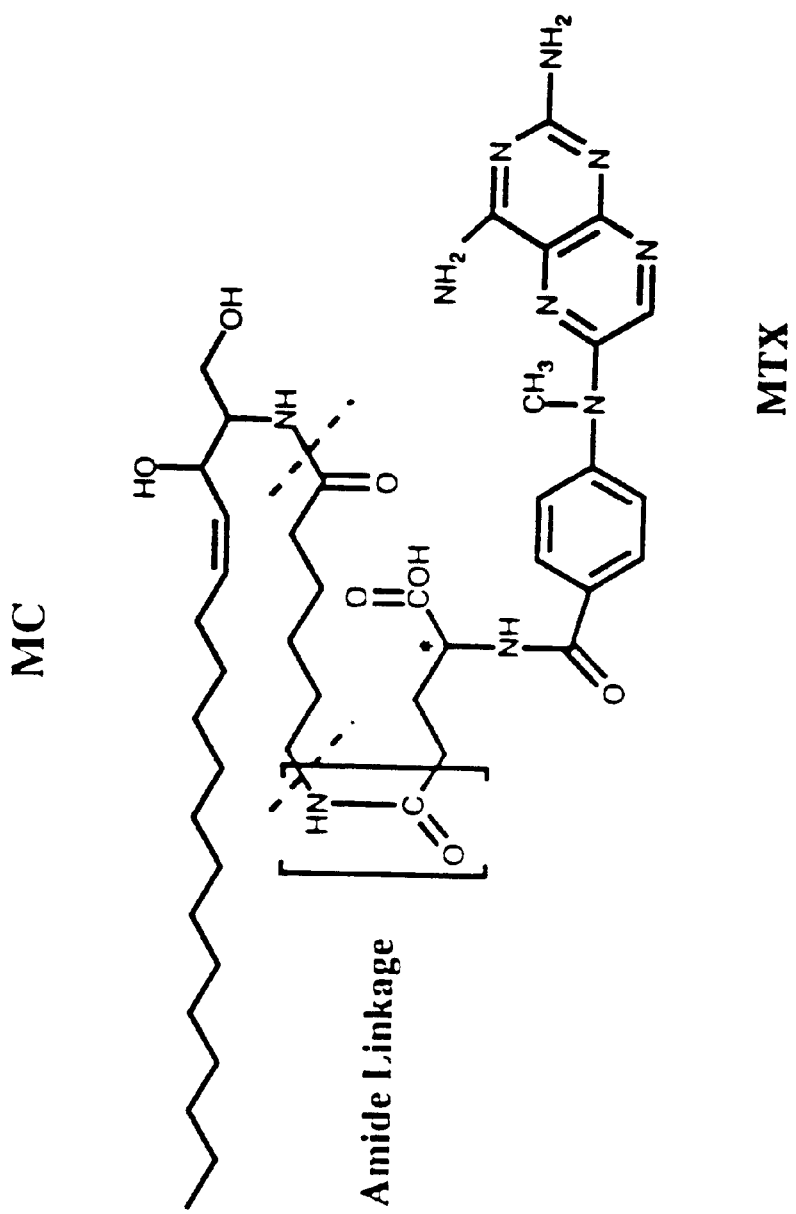
FIGS. 9A through 9D depict prodrugs tested as in Example 9.
Figure 9B:
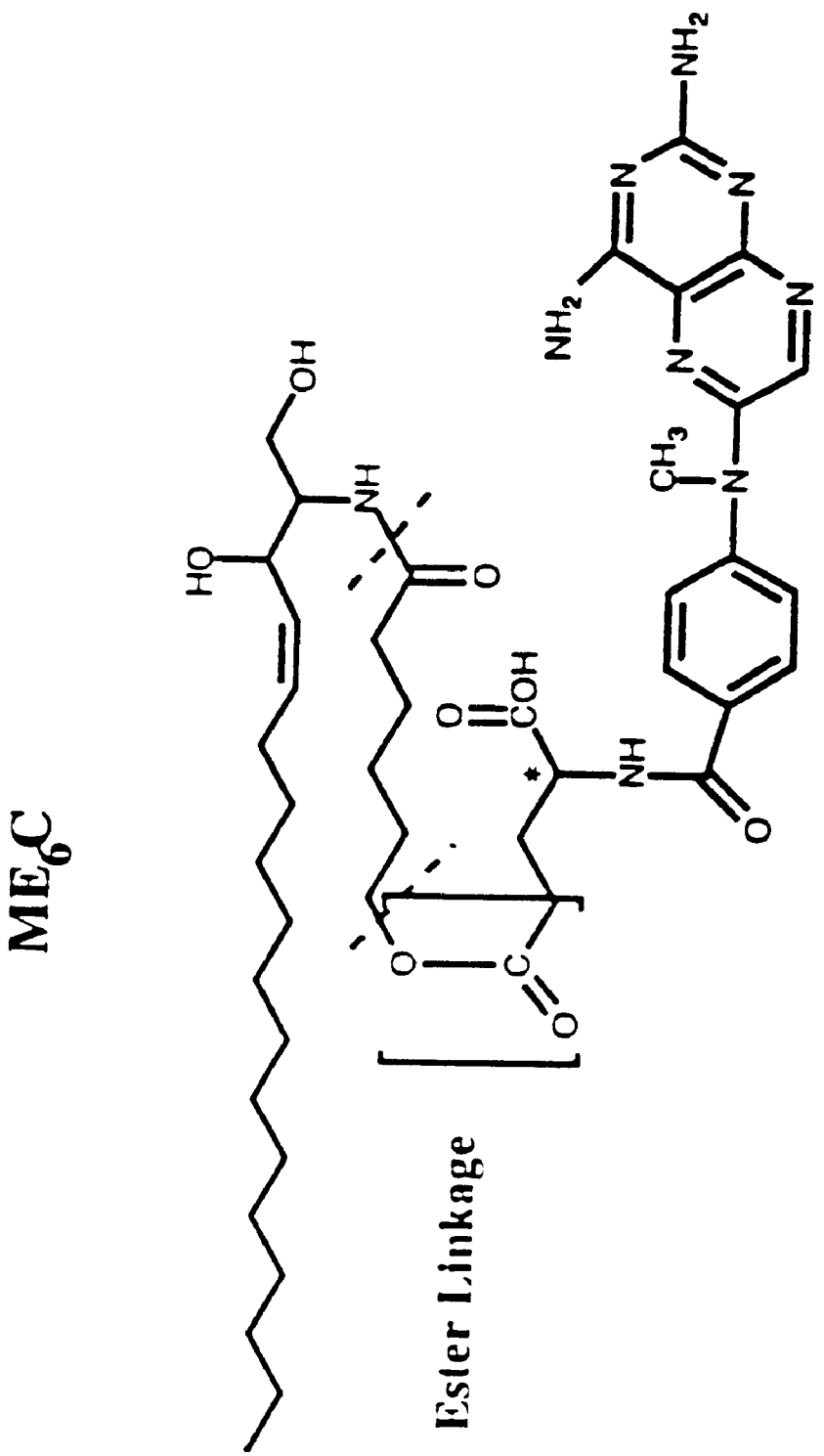
Figure 9C:
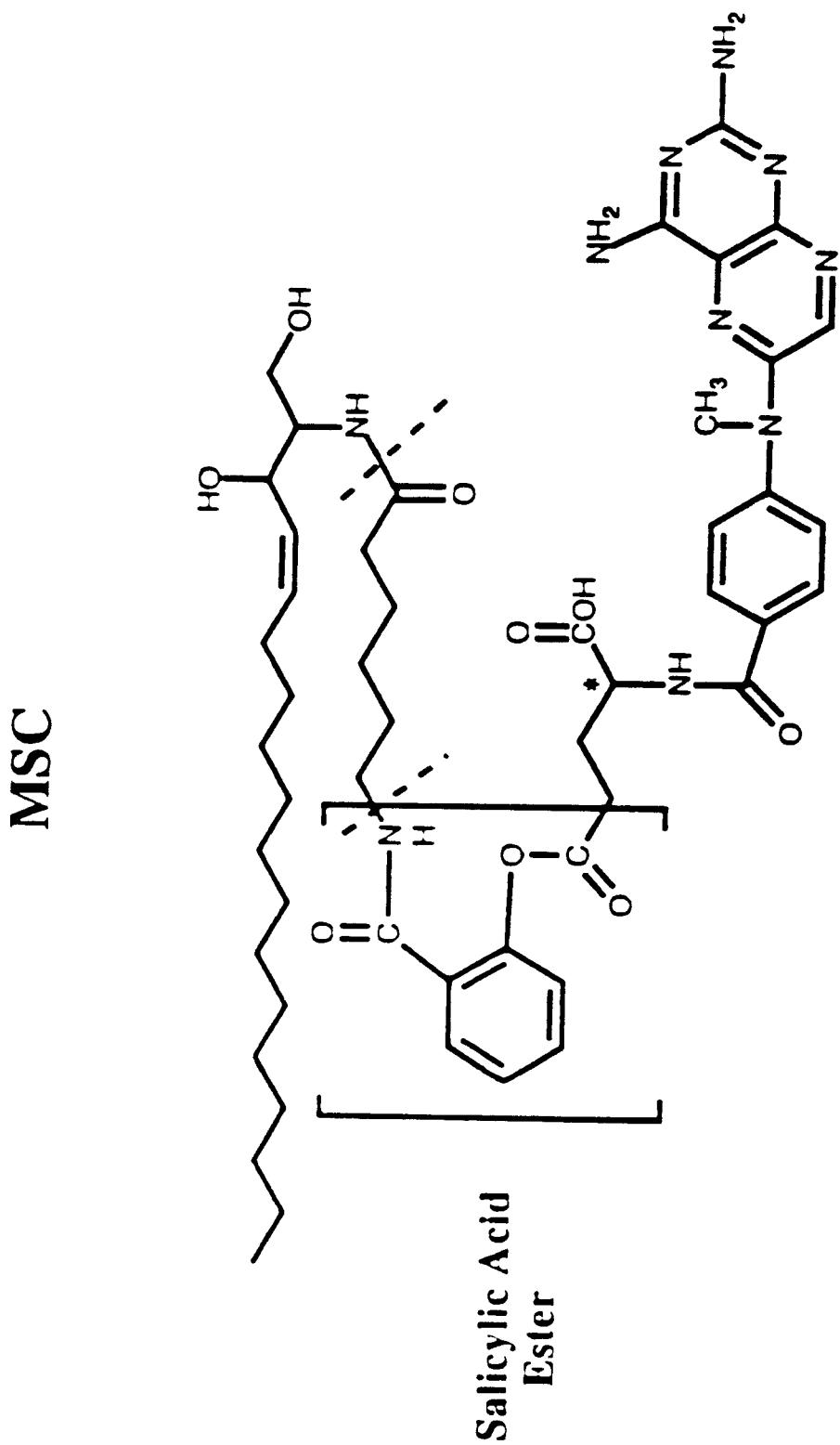
Figure 9D:
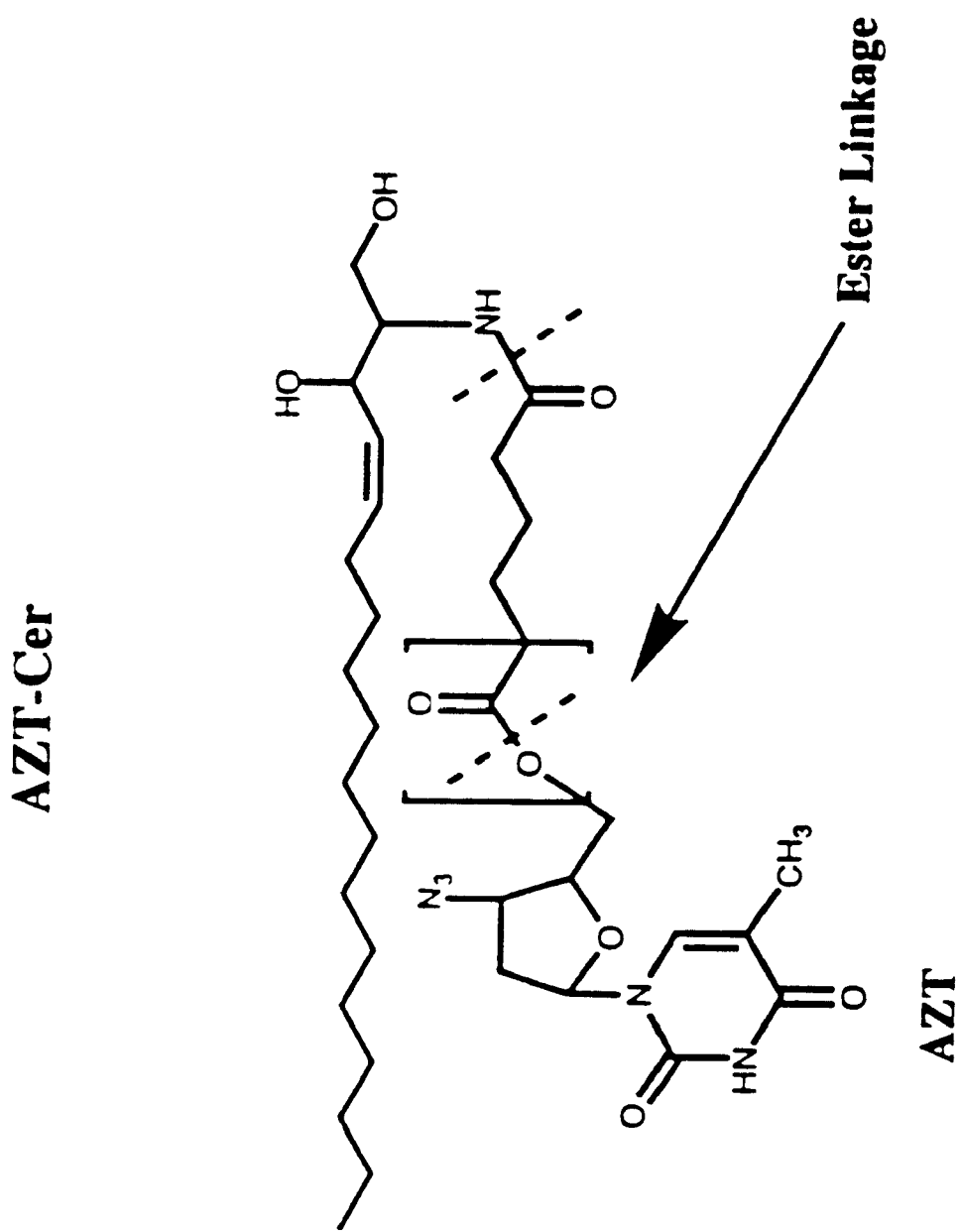

The effect of presenting a biologically active compound such as a drug to mammalian cells as a prodrug covalently linked to a polar lipid carrier moiety was determined as follows. The antifolate drug methotrexate was conjugated with a variety of polar lipid carriers via organic spacer moieties having specific reactive functional groups. A representative sample of such compounds is shown in FIGS. 9A through 9C, wherein MC represents Mtx linked to sphingosine via an amide bond to a 6-aminohexanoic acid spacer, $ME_6C$ represents Mtx linked to sphingosine via an ester linkage to a 6-hydroxyhexanoic acid spacer, and MSC represents Mtx linked to sphingosine via a salicylic acid ester linkage to a 6-aminohexanoic acid spacer. Also studied was a conjugate of azidothymidine linked to sphingosine via an ester linkage to a 6-hydroxyhexanoic acid spacer (N-AZT-ceramide; FIG. 9D). The compounds were tested for their growth inhibitory effects on murine NIH 3T3 cells growing in cell culture. About one million such cells per P100 tissue culture plate were grown in DMEM media supplemented with 10% fetal calf serum (GIBCO, Grand island, N.Y.) in the presence or absence of a growth-inhibitory equivalent of each prodrug. Cell numbers were determined after 70 hours growth in the presence or absence of the prodrug. In a second set of experiments was included in the growth media an amount of a brain homogenate containing an enzymatically-active esterase.

The results from these experiments are shown in Table I. As can be seen from these data, the MC prodrug had no effect on the growth and survival of the cells. This result did not change upon co-incubation with the esterase-containing brain extract, which was expected due to the nature of the drug/spacer linkage (an amide bond). A different result was obtained with the $ME_6C$ conjugate. The prodrug was ineffective in inhibiting cell growth or survival in the absence of brain extract. Upon addition of the brain extract, a significant increase in Mtx cytotoxicity was observed. This is consistent with cleavage of the ester linkage by the brain extract-derived esterase. A similar result was obtained with the MCS conjugate, indicating that the brain extract esterase activity was capable of cleaving the salicylic acid ester.

Table II shows the results of drug uptake studies performed with the prodrug N-AZT-ceramide. Antiviral amounts of the prodrug conjugate were added to NIH 3T3 cell cultures, and the antiviral activity of the prodrug was found to be equivalent to the activity of free AZT. In addition, upon removal of the prodrug, intracellular retention of prodrug was found to be up to 15-fold higher than free AZT (Table II) over a 23 h period.

These results indicate that for Mtx-containing conjugates, the free drug must be released from the prodrug for biological activity. These results suggest that specific release of this drug, and perhaps others, can be achieved using cleavable linker moieties that are specifically cleaved only in pathogen-infected cells.

TABLE I

| Sample[1] | # cells/plate[2] | Sample[3] | # cells/plate[4] |
|---|---|---|---|
| Control/FBS | $7.8 \times 10^6$ | Control/FBS | $13 \times 10^6$ |
| $ME_6C$/FBS | $6.5 \times 10^6$ | MSC/FBS | $2.1 \times 10^6$ |
| $ME_6C$/brain | $2.7 \times 10^6$ | MSC/brain | $0.51 \times 10^6$ |
| Mtx/FBS | $0.16 \times 10^6$ | Mtx/FBS | $0.13 \times 10^6$ |
| Mtx/brain | $0.09 \times 10^6$ | Mtx/brain | $0.06 \times 10^6$ |
| Control/brain | N.D. | Control/brain | $6.2 \times 10^6$ |

[1]cells incubated with drug/FBS or drug/brain extract for 1 hour at 37° C.
[2]cell growth and survival determined 70 hours after drug addition
[3]cells incubated with drug/FBS or drug/brain extract for 2 hours at 37° C.
[4]cell growth and survival determined 72 hours after drug addition

TABLE II

| Time[1] | AZT[2] | N-AZT-Ceramide[2] |
|---|---|---|
| 0 hr. | 6.49 | 8.45 |
| 23 hr. | 0.55 | 7.78 |

[1]time between the end of drug treatment and assay for intracellular drug concentration
[2]$nM/10^6$ cells

EXAMPLE 10

Figure 10:
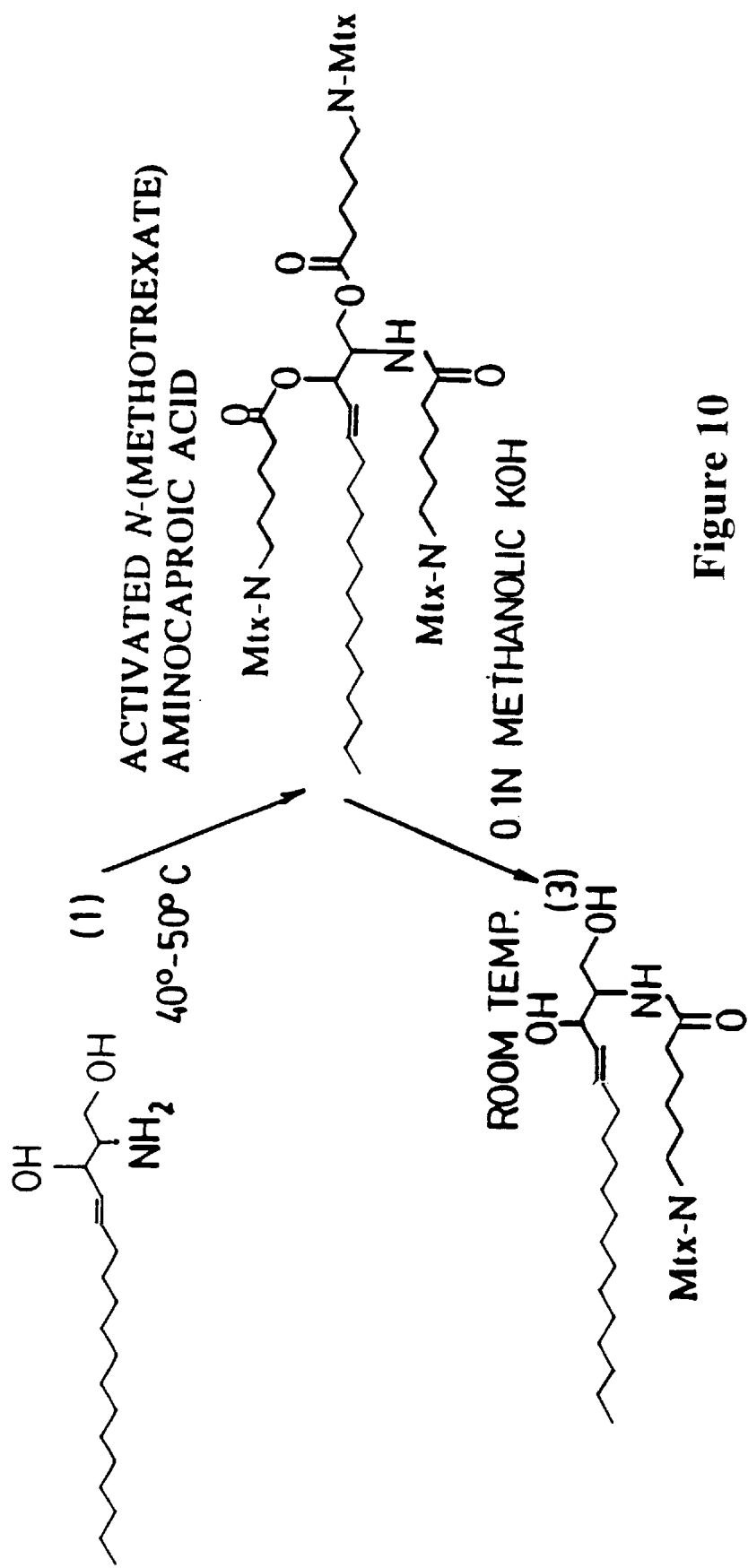
FIG. 10 depicts the synthetic scheme put forth in Example 10.

An antiproliferative agent is prepared wherein the antiproliferative drug methotrexate (Mtx) is conjugated to sphingosine via a 6-aminocaproic acid spacer. This reaction scheme is illustrated in FIG. 10. The primary amino and hydroxyl groups of sphingosine are acylated by reaction with activated N-(methotrexate)aminocaproic acid overnight at 40–50° C., followed by base hydrolysis in 0.1N methanolic KOH. The Mtx derivative of 6-aminocaproic acid is synthesized by activating the carboxylic acid moiety of Mtx and reacting with 6-aminocaproic acid for 2 days at 60–70° C. This reaction is stopped under acidic conditions to liberate anhydrides that form under these conditions.

EXAMPLE 11

An in vivo mouse skin model system was used to demonstrate the use of embodiments of the polar lipid conjugates of the invention for introducing biologically-active compounds through the epidermal layer of the skin and into the underlying skin layers.

In these experiments, various embodiments of the polar lipids of the invention were conjugated to a fluorescent compound, (7-nitro-2-1,3-benzoxadiazol4-yl)-hexanoate (NBD), conjugation being achieved using the methods disclosed herein (Example 10). The NBD-polar lipid conjugates were mixed with dimethylsulfoxide (DMSO), and 20 µL of a 1.7% solution of each conjugate in DMSO were applied to shaved mouse skin and allowed to penetrate the skin for 4 hours. After the 4 hour incubation, skin sections were excised and prepared for light or fluorescence microscopy, using standard histological techniques.

The results of these experiments are shown in FIGS. 11 through 19. In each Figure, the outer layer of the epidermis is located in the upper, left-hand corner of the photomicrograph.

Figure 11:
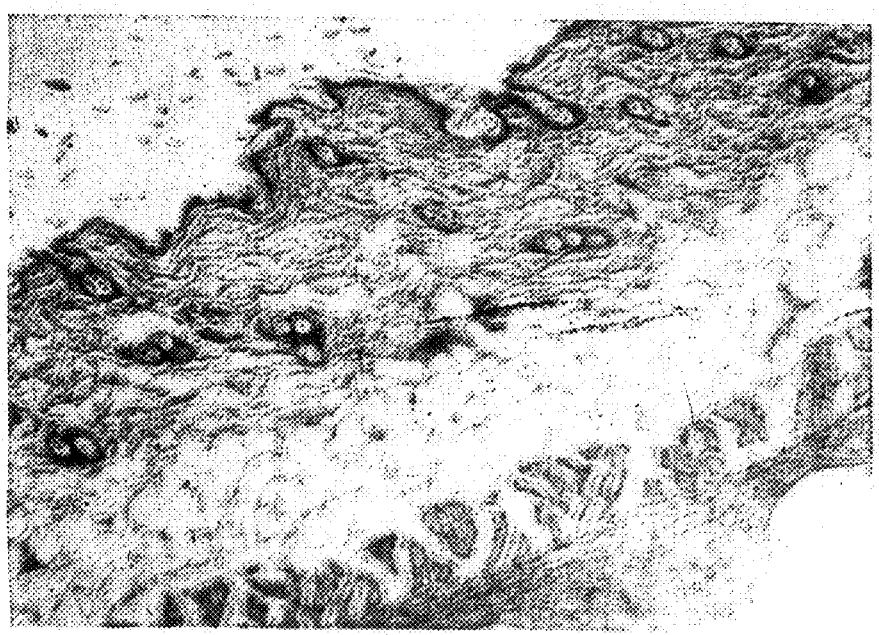
FIGS. 11 through 19 illustrate targeting of polar lipid-conjugated biologically active compounds to skin.

FIG. 11 is a photomicrograph that illustrates hematoxylin-eosin (H&E) staining of mouse skin, observed by light microscopy under 100×magnification. It was observed in this photomicrograph that H&E staining was concentrated in the epidermis and reticular dermis, and that the papillary dermis remained relatively unstained.

Figure 12:

In comparison, FIG. 12 is a fluorescence photomicrograph that illustrates ceramide-NBD staining of mouse skin, observed by fluorescence microscopy under 100× magnification. In this Figure it was observed that the ceramide-NBD fluorescence was carried through the stratum granulosum and epidermis. No partitioning into keratinocytes or Langerhans cells was observed, but distribution through the skin section appeared to be cell-dependent, that is, fluorescence was evenly distributed throughout the cells in the section, rather than being distributed nonspecifically through the microscopic field of view.

Figure 13:
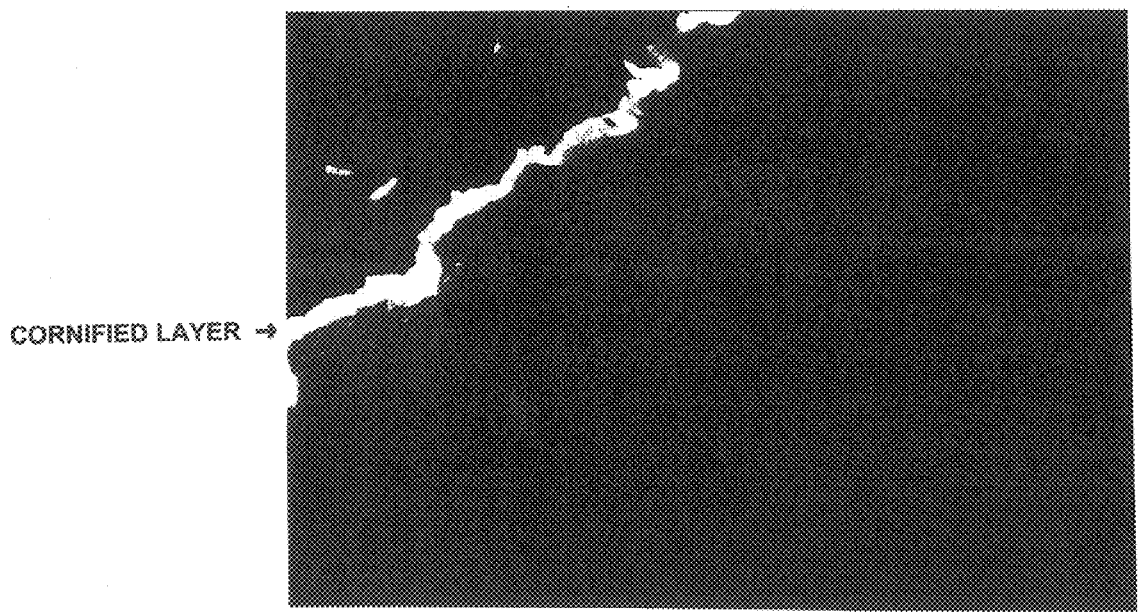
Figure 14:
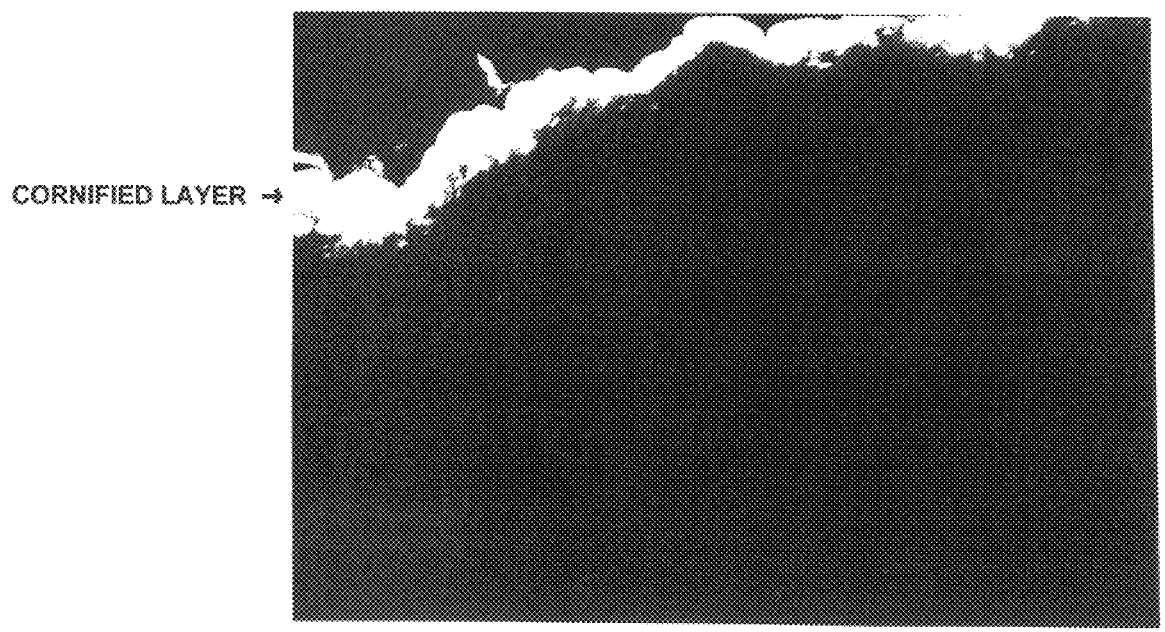
Figure 15:
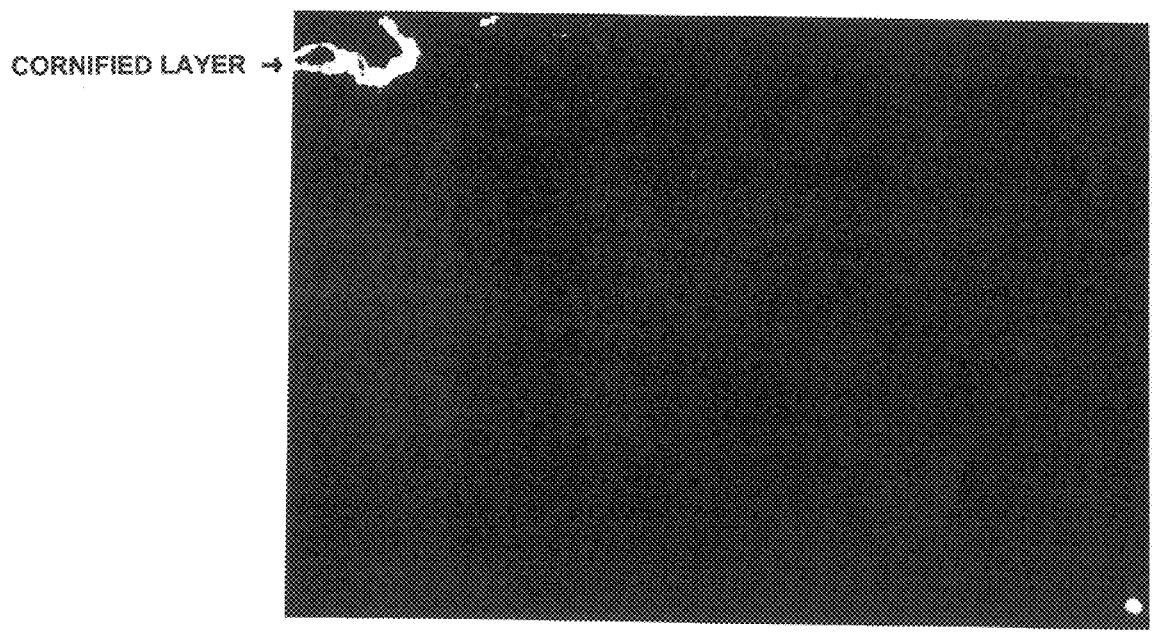

FIG. 13 is a fluorescence photomicrograph that illustrates phosphatidylcholine-NBD staining of mouse skin, observed by fluorescence microscopy under 100×magnification. FIG. 14 is a fluorescence photomicrograph that illustrates phosphatidylethanolamine-NBD staining of mouse skin, observed by fluorescence microscopy under 100× magnification, and FIG. 15 is a fluorescence photomicrograph that illustrates phosphatidylserine-NBD staining of mouse skin, observed by fluorescence microscopy under 100×magnification. Each of these conjugates was observed to result in localized fluorescence in the outer layers of the skin. In FIGS. 13 and 15, some staining of specific areas below the epidermis was also observed, and the compound of FIG. 15 was observed to penetrate into the papillary dermis.

Figure 16:
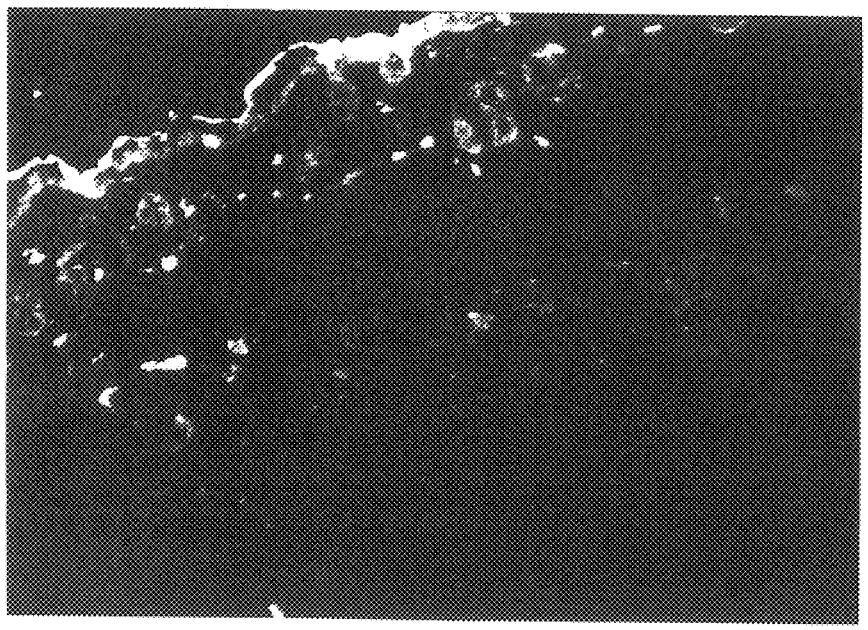

FIG. 16 is a fluorescence photomicrograph that illustrates 1-R{6[(7-nitro-2-1,3-benzoxadiazol-4-ethylamino) caproyl}-NBD (termed phospho-rac-(1-glycerol)-NBD (caproyl)) staining of mouse skin, observed by fluorescence microscopy under 100×magnification. It was observed that the phospho-rac-(1-glycerol)-NBD(caproyl) conjugate penetrated the skin extensively, but in a pattern distinct and different from ceramide-NBD shown in FIG. 12. It was observed that the ceramide-NBD distributed through the cell structure of the deeper skin layers, while the phospho-rac-(1-glycerol)-NBD(caproyl) conjugate concentrated mainly in plasma membranes of fat cells, as well as in some unidentified structures.

Figure 17:
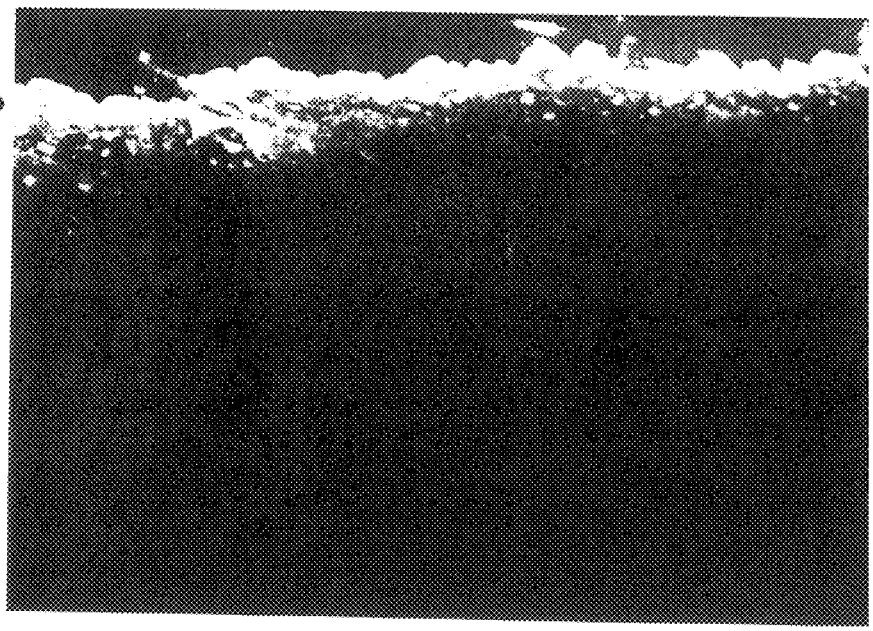

FIG. 17 is a fluorescence photomicrograph that illustrates phosphatidylserine-NBD staining of mouse skin, observed by fluorescence microscopy under 100×magnification. The compound used in FIG. 17 differs from the phosphatidylserine-NBD conjugate shown in FIG. 15 in that the NBD dye is conjugated to the polar lipid via a dodecanoyl moiety in the compound of FIG. 17 and via a caproyl moiety in the compound of FIG. 15. In contrast to the results obtained with the compound of FIG. 15, the dodecanoyl-conjugated NBD compound of FIG. 17 penetrated into the cornified layer, with only minimal penetration into the epidermis.

Figure 18:
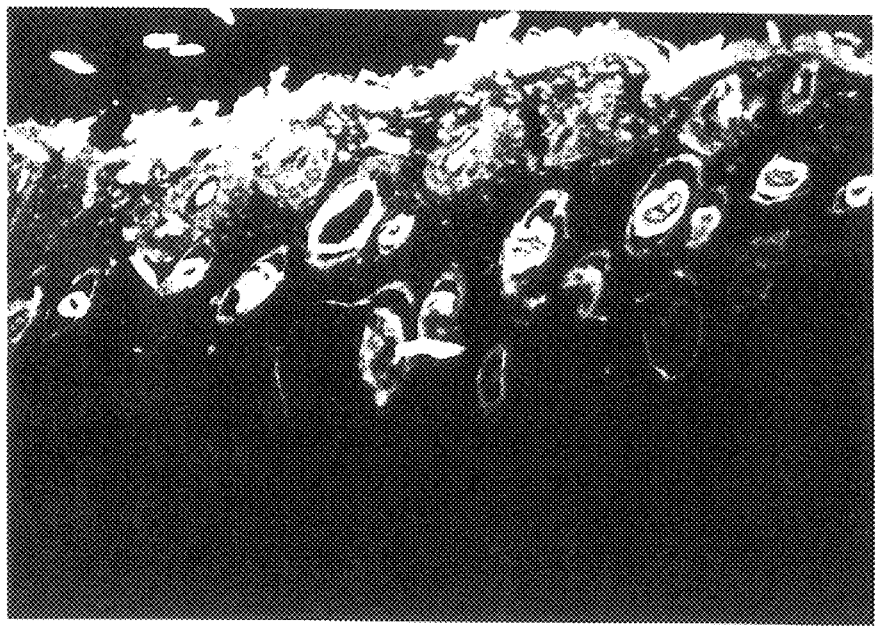

FIG. 18 is a fluorescence photomicrograph that illustrates 1-R(12{(7-nitro-2-1,3-benzoxadiazol-4-ethylamino) }dodecanoyl-NBD (termed phospho-rac-(1-glycerol)-NBD (dodecanoyl)) staining of mouse skin, observed by fluorescence microscopy under 100×magnification. This compound is related to the compound of FIG. 16, but differs in the size of the acyl chain to which the fluorescent NBD label is conjugated; here, it is a dodecanoyl chain, while in FIG. 16 it is a caproyl chain. Both the compound of FIG. 16 and the instant compound were observed to penetrate the papillary dermis and the reticular dermis. In addition, the dodecanoyl-containing compound of FIG. 18 was also observed to accumulate in hair follicles.

Figure 19:
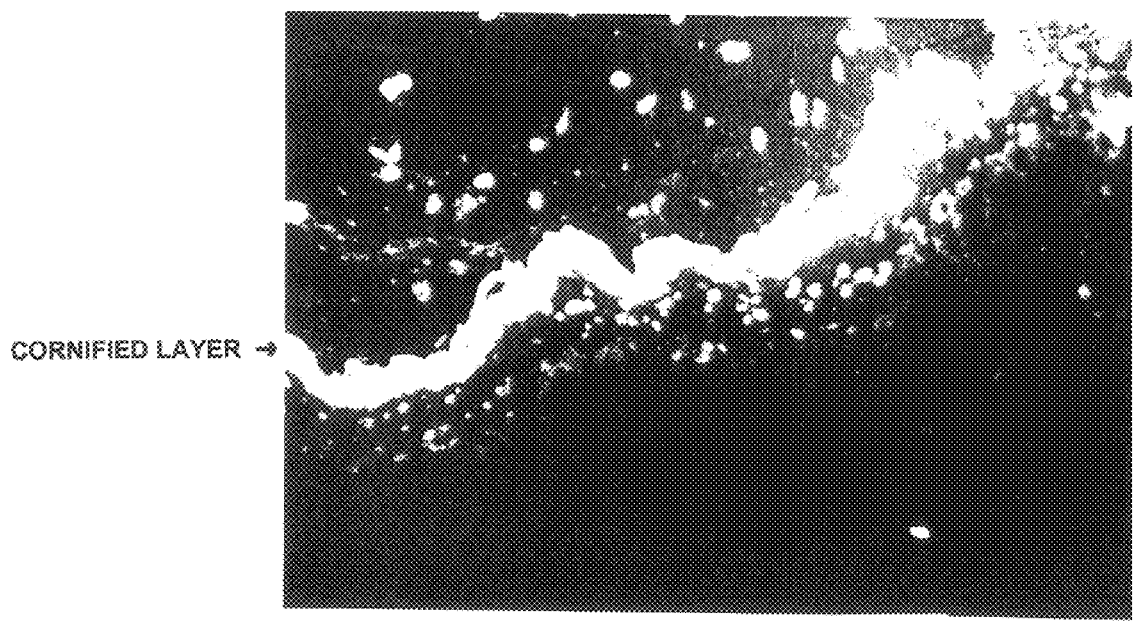

FIG. 19 is a fluorescence photomicrograph that illustrates phosphatidylethanolamine-NBD staining of mouse skin, observed by fluorescence microscopy under 100× magnification. The compound used in FIG. 19 differs from the phosphatidylethanolamine-NBD conjugate shown in FIG. 14 in that the NBD dye is conjugated to the polar lipid via a dodecanoyl moiety in the compound of FIG. 19 and via a caproyl moiety in the compound of FIG. 14. In contrast to the results obtained with the compound of FIG. 14, the dodecanoyl-conjugated NBD compound of FIG. 19 penetrated into the dermis.

Since all compounds were administered in the DMSO vehicle, lack of penetration of some compounds into some or most skin layers discounts the possibility that the DMSO vehicle was responsible for non-specifically carrying fluorophore into the tissue.

These results demonstrate that certain of these conjugates showed specific partitioning into defined layers of the skin. Ceramide-NBD, phospho-rac-(1-glycerol)-NBD(caproyl) and phospho-rac-(1-glycerol)-NBD(docecanoyl) penetrated the skin to the reticular dermis. Caproyl-conjugated phosphatidylethanolamine-NBD, in contrast, did not penetrate beyond the outermost layers of the epidermis, while dodecanoyl-conjugated phosphatidylethanolamnine-NBD was observed to penetrate into the dermis. On the other hand, caproyl-conjugated phosphatidylserine-NBD penetrated into the papillary dermis, while dodecanoyl-conjugated phosphatidylethanolamine-NBD did not penetrate past the cornified layer of the epidermis. These results suggested that polar lipid composition is a determinant in the penetrating ability of the conjugates of the invention, and demonstrated that linkage to polar lipids produced increased penetration of the skin by non-penetrating compounds. These results also demonstrated that the conjugates of the invention partitioned selectively in skin layers and cells, depending on the lipid carrier used in the conjugate. These results further indicate that conjugating antiproliferative compounds of the invention with polar lipids can be used to deliver drugs to specific areas of the skin in greater quantity and concentration than can currently be achieved, and that such drugs can be maintained in specific areas and cells in the skin for longer periods of time. As a consequence of lipid-drug formulation, release of active drug from these conjugates can be achieved by the use of hydrolyzable bonds between drug and carrier.

The specific partitioning of the conjugates of the invention, achieved through the use of polar lipid conjugates, also permits a greater therapeutic index to be achieved. These capacities of the antiproliferative drug conjugates of the invention have important applications to the delivery of medicinal compounds into the skin to treat a variety of pathological conditions. Medicinal salves and ointments for topical treatment purposes are known in the prior art for the treatment of a variety of pathological conditions, but they suffer from non-specific deposition of the antiproliferative drug into both healthy and affected portions of the skin. In addition, appropriate concentrations of topically-applied antiproliferative drugs are currently limited by the escape of the active agent(s) into the systemic circulation, with deleterious effects on other tissues and organs. An example of such a situation is the use of the drug methotrexate to treat psoriasis, where the amount of methotrexate that is capable of being topically applied is limited by hepato- and nephrotoxicity caused by systemic escape of the compound from the skin.

One advantage of the methotrexate-containing embodiments of conjugates of the invention (such as methotrexate ceramide ester, $ME_6C$), is that this compound does not concentrate in the liver or kidney to the same extent as free drug, even upon escape into the systemic circulation.

Similarly, treatment of fungal infections in the skin is limited by systemic hepatotoxicity of many topically-applied antifungal agents, such as ketoconazole, griseofulvin, and ciclopixox. Specific localization of such compounds to the skin using polar lipid-drug conjugates of the invention provides a means of increasing the dosages of such antifungal agents that can be topically applied. Other uses of the conjugates of the invention include treatment of precancerous lesions with polar lipid conjugated 5-fluorouracil.

The present invention therefore solves a problem common to treatment of a variety of pathological conditions in skin tissue with topically-applied salves, ointments or similar medicaments.

It should be understood that the foregoing disclosure emphasizes certain specific embodiments of the invention and that all modifications or alternatives equivalent thereto are within the spirit and scope of the invention as set forth in the appended claims.

What is claimed is:

1. A pharmaceutical composition comprising a corticosteroid drug, a polar lipid carrier, two linker functional groups and a spacer, wherein the spacer has a first end and a second end and wherein the polar lipid is attached to the first end of the spacer through a first linker functional group and the drug is attached to the second end of the spacer through a second linker functional group, the composition further comprising a medicinal ointment or salve.

2. The pharmaceutical composition of claim 1 wherein the drug is selected from the group consisting of cortisone, cortisol, hydrocortisone, prednisone, fluorinated corticosteroids, dexamethasone, alcloethasone, fluoroandrenolide and mometasone.

3. A pharmaceutical composition according to claim 1 wherein the spacer allows the drug to act without being released at an intracellular site and wherein the first linker functional group attached to the first end of the spacer is strong and the second linker functional group attached to the second end of the spacer is weak.

4. A pharmaceutical composition according to claim 1 wherein the spacer allows the facilitated hydrolytic release of the drug at an intracellular site and wherein the first linker functional group attached to the first end of the spacer is strong and the second linker functional group attached to the second end of the spacer is weak.

5. A pharmaceutical composition according to claim 1 wherein the spacer allows the facilitated enzymatic release of the drug at an intracellular site and wherein the first linker functional group attached to the first end of the spacer is strong and the second linker functional group attached to the second end of the spacer is weak.

6. A pharmaceutical composition according to claim 1 wherein the polar lipid is acyl carnitine, acylated carnitine, sphingosine, ceramide, phosphatidyl choline, phosphatidyl glycerol, phosphatidyl ethanolamine, phosphatidyl inositol, phosphatidyl serine, cardiolipin or phosphatidic acid.

7. A pharmaceutical composition according to claim 1 wherein the spacer is a cleavable linker moiety that is specifically cleaved inside a mammalian skin cell.

8. The pharmaceutical composition of claim 7 wherein the cleavable linker moiety is chemically cleaved inside a mammalian skin cell.

9. The pharmaceutical composition of claim 7 wherein the cleavable linker moiety is a substrate for a protein having an enzymatic activity, said protein being specifically expressed in a mammalian skin cell.

10. A pharmaceutical composition according to Claim 1 wherein the spacer is a peptide of formula (amino acid)$_n$, wherein n is an integer between 2 and 25, and wherein the peptide comprises a polymer of one or more different amino acids.

* * * * *